US012673875B2

(12) United States Patent
Sartipi et al.

(10) Patent No.: US 12,673,875 B2
(45) Date of Patent: Jul. 7, 2026

(54) METHOD OF SYNTHESIZING A MOLECULAR SIEVE OF MWW FRAMEWORK TYPE

(71) Applicant: ExxonMobil Chemical Patents Inc., Baytown, TX (US)

(72) Inventors: Sina Sartipi, Willebroek (BE); Marc H. Anthonis, Hofstade (BE); Aaron W. Peters, New Hope, PA (US); Scott J. Weigel, Allentown, PA (US)

(73) Assignee: Exxonmobil Chemical Patents Inc., Baytown, TX (US)

( * ) Notice: Subject to any disclaimer, the term of this patent is extended or adjusted under 35 U.S.C. 154(b) by 356 days.

(21) Appl. No.: 18/264,271

(22) PCT Filed: Mar. 2, 2022

(86) PCT No.: PCT/EP2022/055235
§ 371 (c)(1),
(2) Date: Aug. 4, 2023

(87) PCT Pub. No.: WO2022/184759
PCT Pub. Date: Sep. 9, 2022

(65) Prior Publication Data
US 2024/0101435 A1 Mar. 28, 2024

Related U.S. Application Data

(60) Provisional application No. 63/155,990, filed on Mar. 3, 2021.

(30) Foreign Application Priority Data

Apr. 13, 2021 (EP) ..................................... 21167971

(51) Int. Cl.
*C01B 39/48* (2006.01)
*B01J 29/70* (2006.01)
(Continued)

(52) U.S. Cl.
CPC ........... *C01B 39/48* (2013.01); *B01J 29/7038* (2013.01); *B01J 35/615* (2024.01); *B01J 35/617* (2024.01);
(Continued)

(58) Field of Classification Search
CPC ..... C01B 39/48; B01J 29/7038; B01J 35/615; B01J 35/617; B01J 35/633; B01J 35/70;
(Continued)

(56) References Cited

U.S. PATENT DOCUMENTS

| | | | |
|---|---|---|---|
| 4,439,409 A | 3/1984 | Puppe et al. | |
| 4,826,667 A | 5/1989 | Zones et al. | |

(Continued)

FOREIGN PATENT DOCUMENTS

| | | |
|---|---|---|
| CN | 111977663 A | 11/2020 |
| EP | 0293032 A2 | 11/1988 |

(Continued)

OTHER PUBLICATIONS

Translation of CN111977663A (Year: 2020).*

(Continued)

*Primary Examiner* — Ali Z Fadhel
(74) *Attorney, Agent, or Firm* — Shook, Hardy & Bacon L.L.P.

(57) ABSTRACT

Disclosed is a method of synthesizing a molecular sieve of MWW framework type, and molecular sieves so synthesized. The method comprises preparing a synthesis mixture for forming a molecular sieve of MWW framework type, said synthesis mixture comprising water, a silicon source, a source of a trivalent element X, a structure directing agent R, a source of alkali or alkaline earth metal cation M, and a source of poly(diallyldimethyl ammonium) cation (PDDA).

17 Claims, 5 Drawing Sheets

(51) Int. Cl.

| | |
|---|---|
| *B01J 35/61* | (2024.01) |
| *B01J 35/63* | (2024.01) |
| *B01J 35/70* | (2024.01) |
| *C07C 2/66* | (2006.01) |

(52) U.S. Cl.
  CPC ............. *B01J 35/633* (2024.01); *B01J 35/70* (2024.01); *C07C 2/66* (2013.01); *B01J 2235/05* (2024.01); *B01J 2235/15* (2024.01); *B01J 2235/30* (2024.01); *C01P 2002/72* (2013.01); *C01P 2002/86* (2013.01); *C01P 2004/03* (2013.01); *C01P 2006/12* (2013.01); *C01P 2006/14* (2013.01)

(58) Field of Classification Search
  CPC ............... B01J 2235/05; B01J 2235/15; B01J 2235/30; C07C 2/66; C01P 2002/72; C01P 2002/86; C01P 2004/03; C01P 2006/12; C01P 2006/14
  See application file for complete search history.

(56) References Cited

U.S. PATENT DOCUMENTS

| | | | |
|---|---|---|---|
| 4,954,325 | A | 9/1990 | Rubin et al. |
| 5,236,575 | A | 8/1993 | Bennett et al. |
| 5,250,277 | A | 10/1993 | Kresge et al. |
| 5,362,697 | A | 11/1994 | Fung et al. |
| 5,453,554 | A | 9/1995 | Cheng et al. |
| 5,827,491 | A | 10/1998 | Emerson et al. |
| 6,077,498 | A | 6/2000 | Diaz et al. |
| 6,756,030 | B1 | 6/2004 | Rohde et al. |
| 7,713,513 | B2 | 5/2010 | Jan et al. |
| 7,842,277 | B2 | 11/2010 | Roth et al. |
| 7,959,599 | B2 | 6/2011 | Matusch |
| 8,110,176 | B2 | 2/2012 | Roth et al. |
| 2015/0360964 | A1 | 12/2015 | Rimer et al. |
| 2019/0151832 | A1* | 5/2019 | Johnson ............... B01J 29/7038 |

FOREIGN PATENT DOCUMENTS

| | | | |
|---|---|---|---|
| WO | 97/17290 | A1 | 5/1997 |
| WO | 00/06493 | A1 | 2/2000 |
| WO | 00/06494 | A1 | 2/2000 |
| WO | 2005/118476 | A1 | 12/2005 |
| WO | 2007/094937 | A1 | 8/2007 |
| WO | 2010/014406 | A1 | 2/2010 |
| WO | 2010/021795 | A1 | 2/2010 |
| WO | 2013/048636 | A1 | 4/2013 |
| WO | 2015/112293 | A1 | 7/2015 |

OTHER PUBLICATIONS

Chen et al., "Controlled direct synthesis of single- to multiple-layer MWWW zeolite", National Science Review, vol. 8, No. 7, Sep. 14, 2020, pp. 1-8.

Delitala et al., "Synthesis of MCM-22 zeolites of different Si/Al ratio and their structural, morphological and textural characterisation", Microporous and Mesoporous Materials, vol. 118, No. 1-3, 2009, pp. 1-10.

Gallego et al., "Nanosized MCM-22 zeolite using simple non-surfactant organic growth modifiers: synthesis and catalytic applications", Chemical Communications, vol. 54, No. 71, Jan. 1, 2018, pp. 1-4.

International Search Report and Written Opinion received for PCT Patent Application No. PCT/EP2022/055235, mailed on May 2, 2022, 9 pages.

Lawton et al., "Zeolite MCM-49: A Three-Dimensional MCM-22 Analogue Synthesized by in Situ Crystallization", The Journal of Physical Chemistry, vol. 100, No. 9, Feb. 29, 1996, 3788-3798.

Schwanke et al., "Lamellar MWW-Type Zeolites: Toward Elegant Nanoporous Materials", Applies Sciences, vol. 8, Sep. 13, 2018. pp. 1-15.

Vuono et al., "Synthesis and characterization of MCM-22 and MCM-49 zeolites", Studies in Surface Science and Catalysis, vol. 154, 2004, pp. 203-210.

Yin et al., "Synthesis of the nanosized MCM-22 zeolite and its catalytic performance in methane dehydro-aromatization reaction", Catalysis Communications, vol. 43, 2014, pp. 218-222.

* cited by examiner

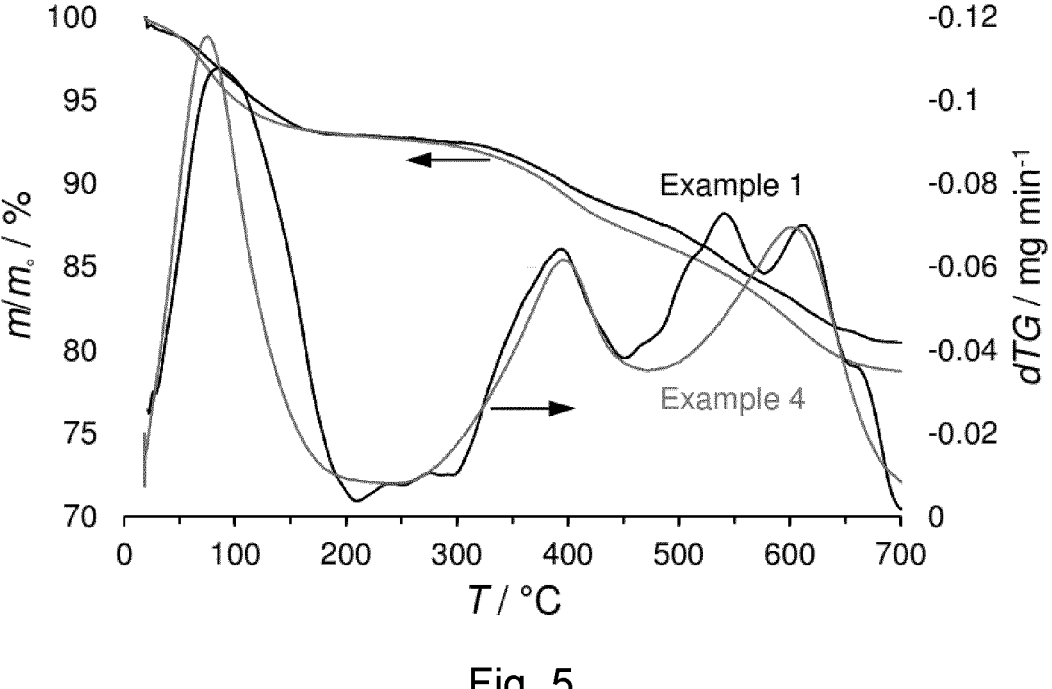
<u>Fig. 5</u>

METHOD OF SYNTHESIZING A MOLECULAR SIEVE OF MWW FRAMEWORK TYPE

CROSS REFERENCE TO RELATED APPLICATIONS

The present application is a National Phase Application claiming priority to PCT Application Serial No. PCT/EP2022/055235 filed Mar. 2, 2022, which claims priority to and the benefit of U.S. Provisional Application No. 63/155,990 filed on Mar. 3, 2021 and of European Patent Application No. 21167971.7, filed on Apr. 13, 2021, U.S. Provisional Application 63/155,990 and European Patent application Ser. No. 21/167,971.7 are hereby incorporated by reference in their entirety.

FIELD OF THE INVENTION

This invention relates to a novel method of synthesizing a molecular sieve of MWW framework type, and molecular sieves so made.

BACKGROUND OF THE INVENTION

Molecular sieve materials, both natural and synthetic, have been demonstrated in the past to have catalytic properties for various types of hydrocarbon conversion reactions. Certain molecular sieves, such as zeolites, AlPOs, and mesoporous materials, are ordered, porous crystalline materials having a definite crystalline structure as determined by X-ray diffraction (XRD). Certain molecular sieves are ordered and produce specific identifiable XRD patterns, but are not strictly crystalline. Within certain molecular sieve materials there may be a large number of cavities, which may be interconnected by a number of channels or pores. These cavities and pores are uniform in size within a specific molecular sieve material. Because the dimensions of these pores are such as to accept for adsorption molecules of certain dimensions while rejecting those of larger dimensions, these materials have come to be known as "molecular sieves" and are utilized in a variety of industrial processes.

Such molecular sieves, both natural and synthetic, include a wide variety of positive ion-containing crystalline silicates. These silicates can be described as three-dimensional framework of $SiO_4$ tetrahedra and Periodic Table Group 13 element oxide (e.g. $AlO_4$) tetrahedra. The tetrahedra are typically corner-shared through oxygen atoms with the electrovalence of the tetrahedra containing the Group 13 element (e.g. aluminum, gallium or boron) being charged balanced by the inclusion of a cation, for example a proton, an alkali metal or an alkaline earth metal cation.

Typically, zeolite syntheses involve hydrothermal crystallization from a synthesis mixture comprising sources of all the elements present in the zeolite such as sources of silica but also of alumina etc., and in many cases a structure directing agent and/or a source of hydroxide or fluoride ions. Often, a synthesis mixture is obtained by treating a solution of aluminate and silicate with a compound which acts to cleave Si—O bonds, thus supplying growing crystals with Si and in some cases breaking up amorphous structures. Often, a hydroxide ($OH^-$) source is used to assist in Si—O bond cleavage. Zeolite synthesis also commonly use structure directing agents (SDAs) to help promote the formation of crystals with the desired structure, especially organic molecule structure directing agents. Typically, zeolite crystals form around structure directing agents with the structure directing agent occupying pores in the zeolite once crystallization is complete. The "as-synthesized" zeolite will therefore contain the structure directing agent in its pores so that, following crystallization, the "as-synthesized" zeolite is usually subjected to a calcination step to remove the structure directing agent. For many catalytic applications, it is also desired to include metal cations such as metal cations of Groups 2 to 15 of the Periodic Table of the Elements within the molecular sieve structure. This is typically accomplished by ion exchange treatment. Formation of a desired zeolite structure can also be encouraged by adding seed crystals to the synthesis mixture. Seeding a molecular sieve synthesis mixture can have beneficial effects, including for example controlling product particle size, accelerating synthesis, improving selectivity for the desired structure type, and sometimes avoiding the need for an organic structure directing agent.

Molecular sieves such as zeolite crystal structures have found a wide range of applications within refinery processes and other processes for manipulating petroleum streams. Some zeolite applications are catalytic in nature, while other applications focus on the ability of zeolites to selectively adsorb molecules within a gas stream.

MWW-type molecular sieves are one class of zeolite useful in industrial processes, including for example in catalysis. Some members of the MWW zeolite family are active components of commercial catalysts for processes such as alkylation. MCM-22 has been employed successfully at a commercial scale in alkylation of benzene to produce cumene.

Zeolitic materials designated by the IZA-SC as being of the MWW topology are multi-layered materials which have two pore systems arising from the presence of both 10 and 12 membered rings. As such, MWW-type molecular sieves can be both microporous and mesoporous. As used herein, the term microporous is used to denote materials with pores having a diameter less than 1.5 nm and mesoporous is used to denote materials with pores having a diameter from 1.5 nm to 50 nm. Based on their 10-ring internal pore system, MWW framework type zeolites are considered to be intermediate pore size zeolites, which generally have a pore size from about 5 Å to less than about 7 Å. However, the 12-ring surface pockets, which do not communicate with the 10-ring internal pore system, can impart some properties more similar to large pore zeolite alkylation catalysts, such as mordenite.

Molecular sieves having a MWW framework structure are commonly referred to as a "MWW family molecular sieve material". As used herein, the term "MWW family molecular sieve material" includes one or more of:

(i) molecular sieves made from a common first degree crystalline building block unit cell, in which the unit cell has the MWW framework topology. (A unit cell is a spatial arrangement of atoms which if tiled in three-dimensional space describes the crystal structure. Such crystal structures are discussed in the "Atlas of Zeolite Framework Types", Fifth edition, 2001, the entire content of which is incorporated as reference.);

(ii) molecular sieves made from a common second degree building block, being a 2-dimensional tiling of such MWW framework topology unit cells, forming a monolayer of one unit cell thickness, preferably one c-unit cell thickness;

(iii) molecular sieves made from common second degree building blocks, being layers of one or more than one unit cell thickness, wherein the layer of more than one unit cell thickness is made from stacking, packing, or binding at least two monolayers of one unit cell thickness. The stacking of such second degree building blocks can be in a regular fashion, an irregular fashion, a random fashion, or any combination thereof; and (iv) molecular sieves made by any regular or random 2-dimensional or 3-dimensional combination of unit cells having the MWW framework topology.

The MWW family molecular sieve materials are characterized by having an XRD pattern including d-spacing maxima at 12.4±0.25, 3.57±0.07 and 3.42±0.07 Angstroms (either calcined or as-synthesized). The MWW family molecular sieve materials may also be characterized by having an XRD pattern including d-spacing maxima at 12.4±0.25, 6.9±0.15, 3.57±0.07 and 3.42±0.07 Angstroms (either calcined or as-synthesized). The XRD data used to characterize said molecular sieve are obtained by standard techniques using the K-alpha doublet of copper as the incident radiation and a diffractometer equipped with a scintillation counter and associated computer as the collection system. Materials that belong to the MWW family include, but not limited to, MCM-22 (described in U.S. Pat. No. 4,954,325); PSH-3 (described in U.S. Pat. No. 4,439,409); SSZ-25 (described in U.S. Pat. No. 4,826,667); ERB-1 (described in European Patent No. 0293032); ITQ-1 (described in U.S. Pat. No. 6,077,498); ITQ-2 (described in International Patent Publication No. WO97/17290); ITQ-30 (described in International Patent Publication No. WO2005118476); MCM-36 (described in U.S. Pat. No. 5,250,277); MCM-49 (described in U.S. Pat. No. 5,236,575); MCM-56 (described in U.S. Pat. Nos. 5,362,697, 5,827,491, and 5,453,554); EMM-10 (described in U.S. Pat. No. 8,110,176), EMM-10-P (described in U.S. Pat. No. 7,959,599), EMM-12 (described in International Patent Publication No. WO2010/021795), EMM-13 (described in International Patent Publication No. WO2010/014406), and an MCM-22 family material (described in U.S. Pat. No. 7,842,277). Also, UZM-8 (described in U.S. Pat. No. 6,756,030); and UZM-8HS (described in U.S. Pat. No. 7,713,513). The entire contents of said patents and applications are incorporated herein by reference. WO 2007/094937 discloses a method of manufacturing a molecular sieve of the MCM-22 family. WO 2015/112293 discloses a method for making molecular sieves having a MWW framework structure using precipitated aluminosilicates.

MWW-type zeolites have a lamellar three-dimensional structure, each two-dimensional layer being approximately 1-2 nm thick. Within the MWW family, many individually defined materials represent different stacking arrangements of separated lamellae. Various strategies that have been utilised to obtain different members of the MWW family are reviewed in "Lamellar MWW-Type Zeolites: Toward Elegant Nanoporous Materials", A. Schwanke et al., *Appl. Sci.* 2018, 8, 1636, the contents of which are incorporated herein by reference. For example, MCM-22 can form via the precursor (P)MCM-22 containing the structure directing agent (SDA) hexamethyleneimine (HMI) sandwiched between individual lamellae, with hydrogen bonds between the HMI molecules and silanol groups on the zeolite surface holding lamellae in place. Calcination removes the HMI molecules and condenses the silanol groups, thereby forming three-dimensional MCM-22. A three-dimensional analogue of MCM-22, named MCM-49, can be formed by direct crystallization from a gel mixture, again using HMI as the SDA, by increasing the relative proportion of alkali metal (sodium) in the composition. "Zeolite MCM-49: A Three-Dimensional MCM-22 Analogue Synthesized by in situ Crystallization", S. L. Lawton et al., *J. Phys. Chem.,*

1996, 100, 3788-3798, discloses synthesis and characterization of MCM-22, (P)MCM-22 and MCM-49. It is disclosed that (P)MCM-22 is synthesized when the reaction mixture has an organic template/inorganic cation (alkali metal) ratio of greater than 2.0, whereas MCM-49 forms when the mole ratio is less than 2.0. MCM-22 and MCM-49 were found to be structurally very similar, except that the unit cell c-parameter of MCM-49 is larger, suggesting increased distance between layers in the lamellar structure. Increasing the proportion of alkali metal in the reaction mixture led to increased aluminum incorporation in the zeolite framework. For MCM-49, crystallite framework $Si/Al_2$ ratios of 17-22 were reported with HMI as the SDA. MCM-22 zeolites with Si/Al ratios in the range 9-46 (corresponding to $Si/Al_2$ ratios of 18-92) are disclosed in "Synthesis of MCM-22 zeolites of different Si/Al ratio and their structural, morphological and textural characterisation", C. Delitala et al., *Microporous and Mesoporous Materials*, volume 118, issues 1-3, 2009, pages 1-10.

Preparations of MCM-22 from reaction mixtures using NaOH or KOH as mineralizing agents and HMI as the SDA are disclosed in "Synthesis and characterization of MCM-22 and MCM-49 zeolites", D. Vuono et al., *Studies in Surface Science and Catalysis,* 154, 2004, 203-210. In that study, MCM-49 zeolites were also reported, but only using NaOH as the mineralising agent (only (P)MCM-22 could be obtained using KOH).

Preparation of nanosized MCM-22 zeolite from a synthesis mixture comprising colloidal silica as source of Si and a cationic polymer (poly(diallyldimethyl ammonium) (PDDA) chloride) is disclosed in "Synthesis of the nanosized MCM-22 zeolite and its catalytic performance in methane dehydro-aromatization reaction", X. Yin et al., *Catalysis Communications*, volume 43, 2014, pages 218-222. PDDA chloride was added to play the role of protecting agent to avoid the synthesis colloids self-aggregation.

MCM-56 is an MWW family zeolite with partial lamellae disorder, which forms as an intermediate of MCM-49 (see A. Schwanke et al.). Each layer in MCM-56 is porous and has a framework structure closely related to that of MCM-22 and other MCM-22 family members. MCM-56 is isolated by stopping the reaction used to form MCM-49 in the middle of the crystallization course. If crystallization is allowed to continue, the initially exfoliated, randomly packed MCM-56 sheets (with MCM-22 topology and one 25 Å thick unit cell) become gradually organized into a 3-dimensional framework ordered in the c-direction, which is formally the zeolite MCM-49. The formation of MCM-56 presents a unique challenge, especially on a large scale, because it is a transient product and may undergo further change during the manufacturing process. For example, while careful control of crystallization conditions can be manageable on a laboratory scale, determining the correct time to stop crystallization, and thus isolate a useful quantity of an intermediate zeolite can be problematic on a commercial scale. WO 2013/048636 discloses a method for manufacturing high quality porous crystalline MCM-56 material.

MWW zeolites are characterized by high aluminum content. A high aluminum content is important for high activity in catalytic processes. Each aluminum centre on an accessible part of the zeolite provides an acidic site that may provide catalytic activity. Higher aluminum content makes the zeolite more acidic and thus provides higher activity. When aluminum centres are located in zeolite pores, the size and shape of the pore can influence selectivity and activity. For example, reactant molecules that can access the pores more easily may undergo catalytic reactions in preference to molecules that have a size and/or shape that inhibits access to pores. This can present advantages and limitations in zeolite catalysts. For example, where aluminum centres are incorporated at sites in relatively small pores, the resulting zeolite catalyst may offer high selectivity for reactions with small reactant molecules, but also relatively low activity (even with smaller molecules, for example because reactions are slowed by the time taken for reactant molecules to enter and exit pores). Such catalysts may not be effective in catalysis of reactions involving larger reactant molecules, such as aromatic molecules. In MWW-type zeolites, aluminum centres located in 12-ring surface pores offer potential catalytic sites accessible to relatively large molecules, while aluminum centres located in the 10-ring internal pore network may be accessible only to smaller molecules. The mixed 10-ring/12-ring structure of MWW zeolites can provide catalysts suitable for use with a relatively wide variety of reactant molecules, depending on where aluminum is incorporated into the zeolite framework.

There exists many methods of synthesizing a molecular sieve of MWW framework type, but there remains a need for further MWW zeolites with improved properties or improved combination of properties such as a high external surface area (high mesoporosity) in combination with a high micropore volume.

SUMMARY OF THE INVENTION

The invention provides a method of synthesizing a molecular sieve of MWW framework type, the method comprising preparing a synthesis mixture capable of forming a molecular sieve of MWW framework type, said synthesis mixture comprising water, a silicon source, a source of a trivalent element X, a structure directing agent R, a source of alkali or alkaline earth metal cation M, a source of poly(diallyldimethyl ammonium) cation (PDDA), optionally a source of a pentavalent element Z, optionally a source of hydroxide ions, and optionally seed crystals. The synthesis mixture has the following molar ratio composition: $Si:X_2=8$ to less than 30, $H_2O:Si=5$ to less than 50, $M:Si=0.05$ to 1.0, $R:Si=0.05$ to 1.0. The synthesis mixture comprises the source of PDDA in an amount of from 0.01 to less than 1.0 wt %, based on the weight of the synthesis mixture. The method further comprises heating said synthesis mixture under crystallization conditions for a time sufficient to form crystals of said molecular sieve of MWW framework type, said crystallization conditions including a temperature of from 80° C. to 225° C., and recovering said crystals of the molecular sieve of MWW framework type from the synthesis mixture.

The presence of PDDA in the zeolite synthesis mixture has been found to aid formation of MWW-type molecular sieve having a high external surface area together with a high micropore volume. In particular, the resulting MWW-type molecular sieve appears to have an external surface area in the range of that of previously known MCM-56 zeolite while, in contrast to the latter, it has a higher micropore volume close to that of previously known MCM-49 zeolite. Without wishing to be bound by theory, the inventors believe that the PDDA used in the synthesis mixture acts as a zeolite growth modifier. An increased external surface area is especially advantageous as accessibility to surface pockets of MWW-type molecular sieves is of significant importance for their catalytic performance, for instance in applications such as alkylation while preserving or increasing microporosity is fundamental to shape selective catalysis with molecular sieves.

The invention also provides a molecular sieve of MWW framework type obtainable by or made according to the synthesis method of the invention.

The invention further provides a molecular sieve of MWW framework type having, in its calcined and anhydrous form, a composition comprising the molar relationship: $(n)SiO_2:X_2O_3$ wherein X is a trivalent element selected from the group consisting of aluminum, boron, gallium, and mixtures thereof, and n is the number of moles of $SiO_2$ per mole of $X_2O_3$ and varies from 8 to less than 30; an external surface area $(S_{ext})$ of at least 125 $m^2/g$; and a micropore volume $(V_{micro})$ of more than 0.13 $cm^3/g$.

The invention further provides a catalyst comprising the molecular sieve of MWW framework type of the invention.

The invention further provides a hydrocarbon chemical conversion process comprising the step of contacting a hydrocarbon feedstock with a catalyst of the invention. In one embodiment the catalysis process is alkylation, such as aromatic alkylation.

These and other features and attributes of the present disclosure and their advantageous applications and/or uses will be apparent from the detailed description which follows. It will of course be appreciated that features described in relation to one aspect of the present invention may be incorporated into other aspects of the present invention.

BRIEF DESCRIPTION OF THE DRAWINGS

FIG. 5 shows the thermogravimetric analysis of as-prepared Comparative Example 1 and Example 4.

DETAILED DESCRIPTION

Figure 1:
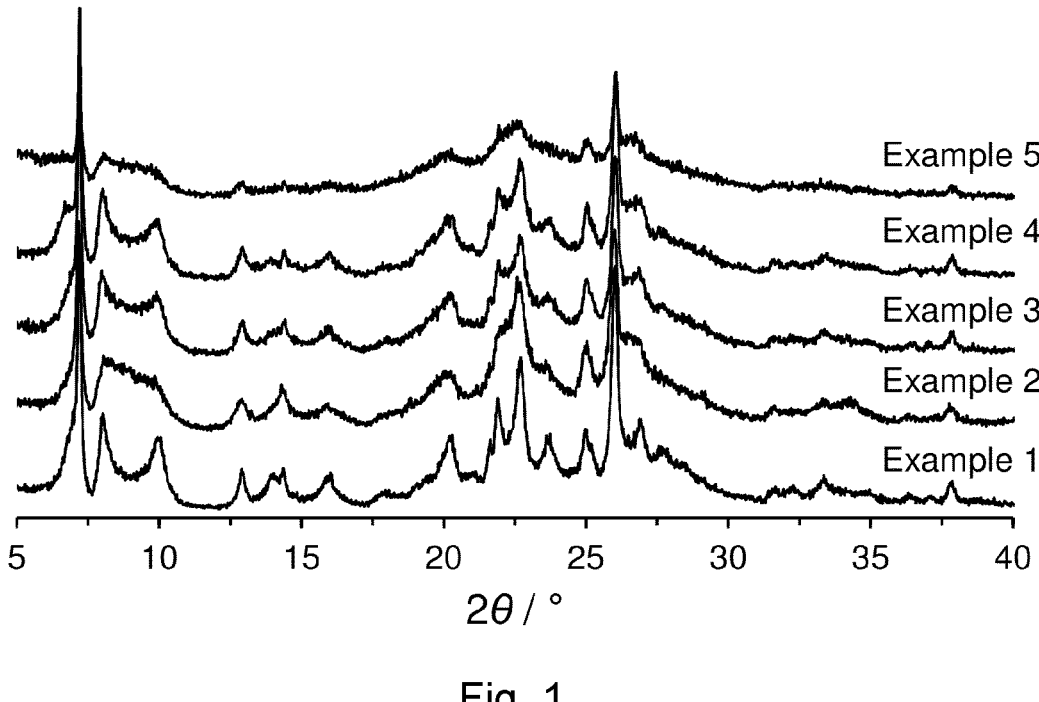
FIG. 1 shows XRD spectra of Comparative Examples 1-2 and Examples 3-5, in their as-synthesized form.
Figure 2A:
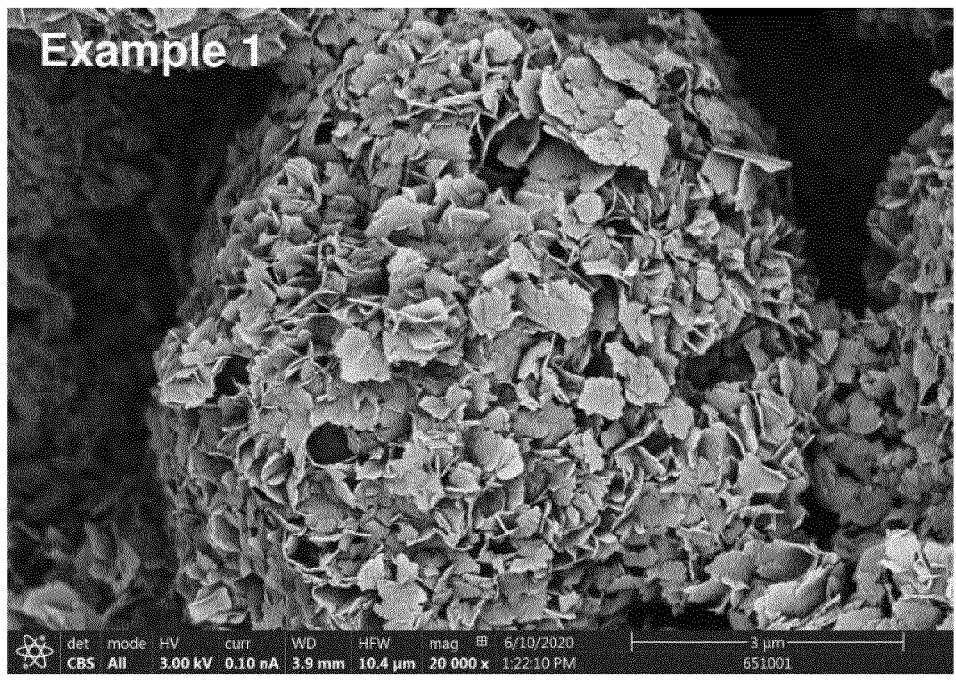
FIGS. 2a-2e show Scanning Electron Microscopy (SEM) images of each of Comparative Examples 1-2 and Examples 3-5.
Figure 2B:
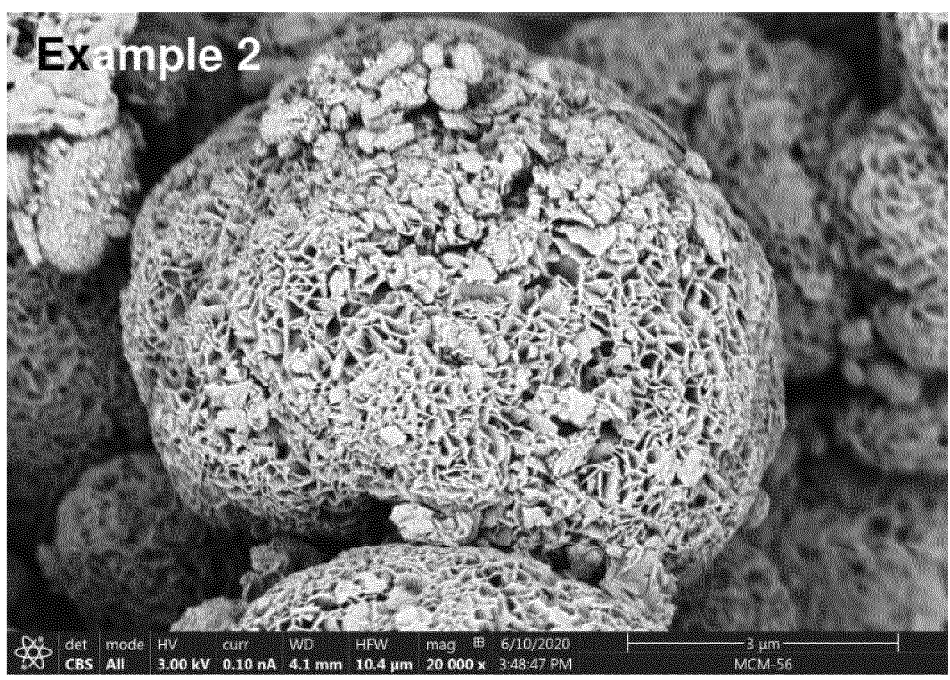
Figure 2C:
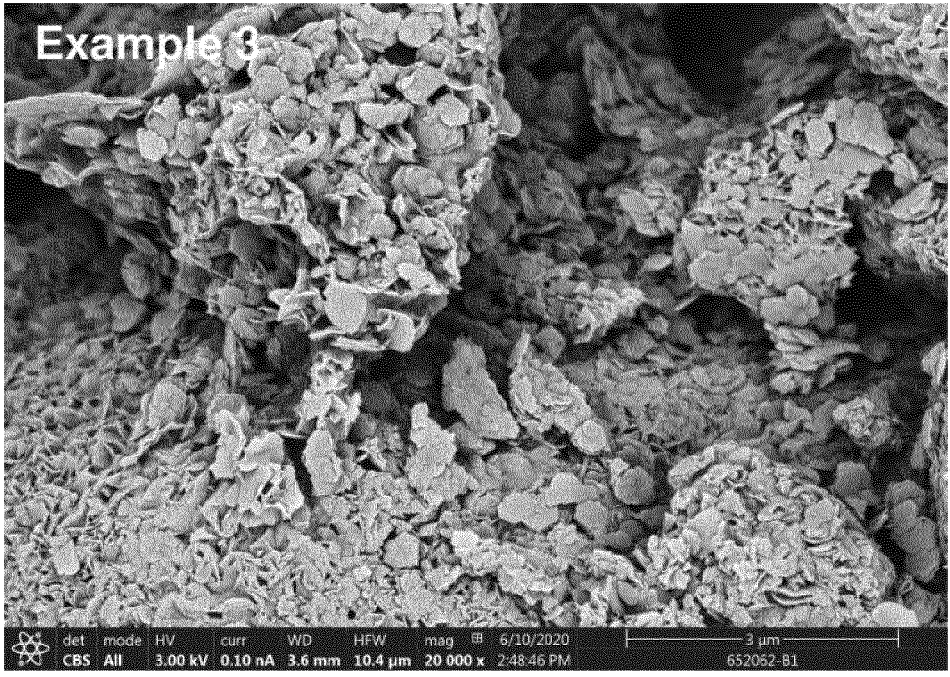
Figure 2D:
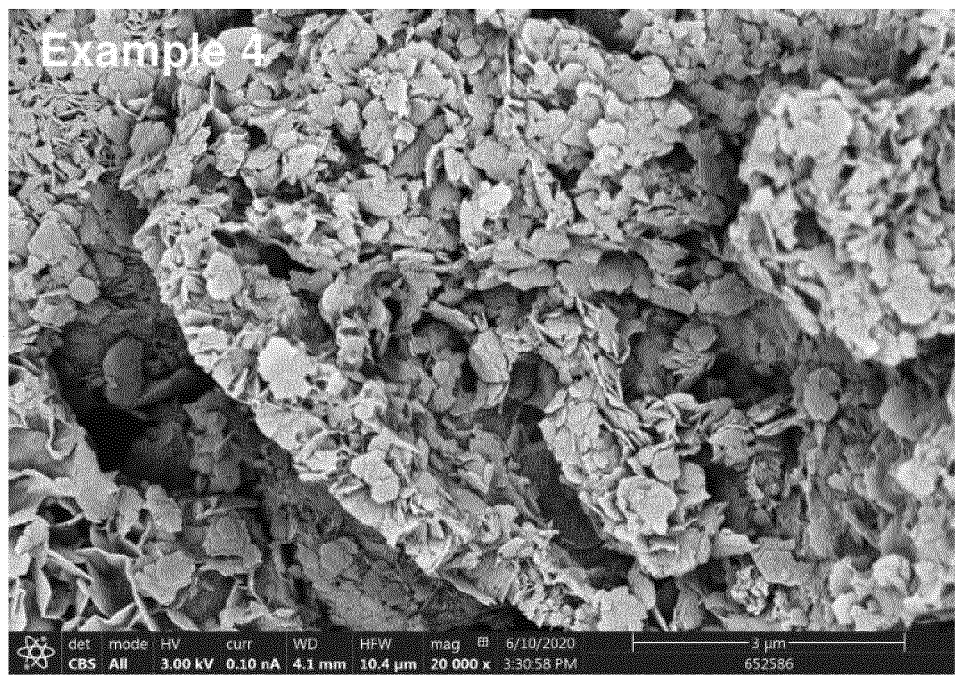
Figure 2E:
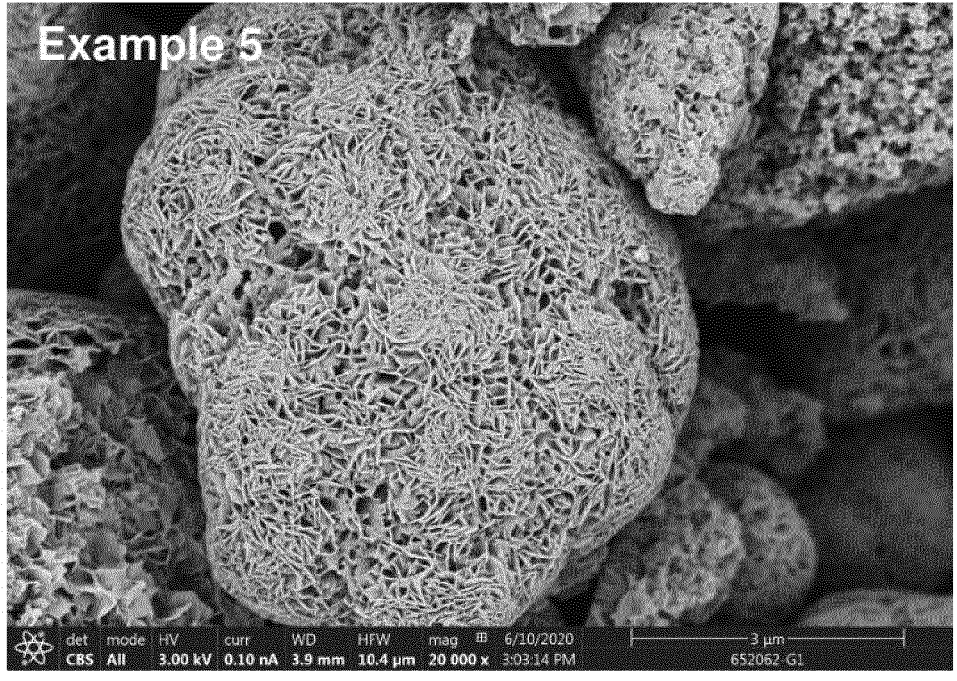

The method of synthesizing a molecular sieve of MWW framework type according to the invention involves preparing a synthesis mixture according to conventional techniques, except that the synthesis mixture comprises at least a source of poly(diallyldimethyl ammonium chloride) cation (PDDA) and that the synthesis mixture has a $Si:X_2$ molar ratio of less than 30 and a $H_2O:Si$ molar ratio of less than 50. The method of synthesizing a molecular sieve according to the invention further involves crystallizing the molecular sieve according to conventional techniques, and isolating the molecular sieve according to conventional techniques.

The Synthesis Mixture

As mentioned above, the synthesis mixture can be prepared according to conventional methods. The components of the synthesis mixture may be combined in any order.

The synthesis mixture of the present invention comprises a cationic polymer, in particular a source of poly(diallyldimethyl ammonium) cation (PDDA). The source of PDDA is present in the synthesis mixture of the present invention in an amount of from 0.01 to less than 1.0 wt %, typically from 0.02 to 0.7 wt %, preferably from 0.04 to less than 0.7 wt %, such as from 0.05 to 0.5 wt %, based on the weight of synthesis mixture. Without wishing to be bound by theory, the inventors believe that said PDDA acts as a zeolite growth modifier, resulting in a modified structure of the zeolite. More particularly, the inventors surprisingly found out that the presence of PDDA in the zeolite synthesis mixture of the present invention aid formation of MWW-type molecular sieve having a high external surface area together with a high micropore volume, the resulting MWW-type molecular sieve having an external surface area in the range of that of previously known MCM-56 zeolite while, in contrast to the latter, it has a higher micropore volume close to that of previously known MCM-49 zeolite. This combination of high external surface area together with high micropore volume is especially advantageous as it results in a higher accessibility to surface pockets of MWW-type molecular sieves (which is of significant importance for their catalytic performance, for instance in applications such as alkylation), while preserving selectivity.

The source of PDDA may for instance be selected from at least one of PDDA chloride and/or PDDA hydroxide, such as PDDA chloride. The molecular weight (Mw) of the source of PDDA is typically in the range of from 50,000 to 1,000,000 grams per mole, preferably from 100,000 to 800,000, such as from 150,000 to 600,000 or from 200,000 to 500,000, specific examples including PDDA sources having a Mw of 200,000-350,000 or 400,000-500,000.

The synthesis mixture further comprises a structure directing agent R. It will be appreciated that any structure directing agent suitable for formation of an MWW-type molecular sieve may be used. Suitable structure directing agents include cyclopentylamine, cyclohexylamine, cyclo-heptylamine, hexamethyleneimine (HMI), heptamethylene-imine, homopiperazine, and combinations thereof. Addition-ally or alternatively, the structure directing agent may be a diquat salt or a diquat hydroxide, such as a pentamethonium salt or hydroxide (e.g. pentamethonium bromide or hydrox-ide), hexamethonium salt or hydroxide (e.g. hexamethonium bromide or hydroxide), and/or a heptamethonium salt or hydroxide (such as heptamethonium bromide or hydroxide). Additionally or alternatively, the structure directing agent may be diethyl-dimethylammonium salt or hydroxide, or N,N,N-trimethyl-1-adamantanammonium salt or hydroxide, or N,N,N-trimethyl-2-adamantanammonium salt or hydrox-ide, e.g. chloride, bromide or hydroxide. Preferably the structure directing agent R is hexamethyleneimine (HMI). The structure directing agent R is present in a molar ratio relative to silicon of R:Si of 0.05 to 1.0, optionally 0.08 to 0.8, such as 0.1 to 0.5 or 0.1 to 0.3, for instance 0.15 to 0.25 or even 0.16 to 0.20.

The synthesis mixture comprises one or more sources of a trivalent element X such as aluminum, boron, and/or gallium, preferably X comprising Al, and more preferably X being Al. Suitable sources of trivalent element X that can be used to prepare the synthesis mixture depend on the element X that is selected. In embodiments where X is aluminum, Al sources (e.g. aluminum oxides) suitable for use in the method include aluminum salts, especially water-soluble salts, such as aluminum sulfate, aluminum nitrate, aluminum hydroxide, sodium aluminate, and aluminum alkoxides such as aluminum isopropoxide, as well as hydrated aluminum oxides, such as boehmite, gibbsite, and pseudoboehmite, and mixtures thereof. In embodiments where X is boron, B sources include boric acid, sodium tetraborate and potas-sium tetraborate. Sources of boron tend to be more soluble than sources of aluminum in hydroxide-mediated synthesis systems. In embodiments where X is gallium, Ga sources include sodium gallate, potassium gallate, and gallium salts such as gallium chloride, gallium sulfate, and gallium nitrate. Preferably, X is Al and the source of aluminum in the synthesis mixture comprises $Al_2O_3$, for example wherein the source of aluminum is sodium aluminate. The synthesis mixture has a $Si:X_2$ molar ratio of at least 8, preferably at least 10, more preferably at least 12, most preferably at least 13, such as at least 15 or at least 16 or at least 17. The synthesis mixture has a $Si:X_2$ molar ratio of less than 30, in particular at most 28 or even at most 25. The synthesis mixture has a $Si:X_2$ molar ratio of 8 to less than 30, for instance of 10 to less than 30 or from 12 to less than 30, such as from 15 to 25. In an especially preferred embodiment, X is Al.

Si sources (e.g. silicon oxides) suitable for use in the method include silicates, e.g., tetraalkyl orthosilicates such as tetramethylorthosilicate, fumed silica, such as Aerosil® (available from Degussa) and Cabosil® (available from DMS), precipitated silica such as Ultrasil® and Sipernat® 340 (available from Evonik), alkali metal silicates such as potassium silicate and sodium silicate, and aqueous colloidal suspensions of silica, for example, that sold by E.I. du Pont de Nemours under the tradename Ludox®, preferably sili-cates, fumed silica, precipitated silica and alkali metal silicates. In a particular embodiment, the silicon source comprises $SiO_2$, preferably the silicon source is $SiO_2$, for instance in the form of fumed silica, precipitated silica or aqueous colloidal suspensions of silica, most often fumed silica or precipitated silica.

Alternatively or in addition to previously mentioned sources of Si and Al, sources containing both Si and Al elements can also be used as sources of Si and Al. Examples of suitable sources containing both Si and Al elements include amorphous silica-alumina gels or dried silica alu-mina powders, silica aluminas, clays, such as kaolin, meta-kaolin, and zeolites, in particular aluminosilicates such as synthetic faujasite and ultrastable faujasite, for instance USY, beta or other large to medium pore zeolites.

Optionally, the synthesis mixture comprises one or more sources of a pentavalent element Z, such as phosphorus. Suitable sources of pentavalent elements Z depend on the element Z that is selected. Preferably, Z is phosphorus. Suitable sources of phosphorus include phosphoric acid, organic phosphates such as triethyl phosphate and tetraethyl-ammonium phosphate, and aluminophosphates. Alterna-tively, the synthesis mixture does not contain any pentava-lent element Z.

The synthesis mixture comprises one or more sources of alkali or alkaline earth metal cation M, wherein M is preferably selected from the group consisting of sodium, potassium, lithium, rubidium, calcium, magnesium and mix-tures thereof, preferably sodium and/or potassium, more preferably sodium. The sodium source, when present, may be sodium hydroxide, sodium aluminate, sodium silicate, sodium aluminate or sodium salts such as NaCl, NaBr or sodium nitrate. The potassium source, when present, may be potassium hydroxide, potassium aluminate, potassium sili-cate, a potassium salt such as KCl or KBr or potassium nitrate. The lithium source, when present, may be lithium hydroxide or lithium salts such as LiCl, LiBr, LiI, lithium nitrate, or lithium sulfate. The rubidium source, when pres-ent, may be rubidium hydroxide or rubidium salts such as RbCl, RbBr, RBI, or rubidium nitrate. The calcium source, when present, may be calcium hydroxide, for example. The magnesium source, when present, may be magnesium hydroxide, for example. The alkali or alkaline earth metal cation M may also be present in the one or more sources of a trivalent element X, such as sodium aluminate, sodium tetraborate, potassium tetraborate, sodium gallate, potas-sium gallate, and/or in the one or more sources of Si, such as potassium silicate and sodium silicate. The synthesis mixture comprises the alkali or alkaline earth metal cation M source in a M:Si molar ratio of 0.05 to 1.0, preferably 0.08 to 0.5, more preferably 0.1 to 0.3, such as 0.1 to 0.25, or more than 0.1 to less than 0.18.

Optionally, the synthesis mixture comprises one or more sources of hydroxide ions, for example selected from the group consisting of alkali metal hydroxides, alkaline earth metal hydroxides, ammonium hydroxide, and mixtures thereof; such as from sodium hydroxide, potassium hydroxide, lithium hydroxide, rubidium hydroxide, calcium hydroxide, magnesium hydroxide, ammonium hydroxide, and mixtures thereof; more often sodium hydroxide, potassium hydroxide, lithium hydroxide, ammonium hydroxide, and mixtures thereof; most often sodium hydroxide and/or potassium hydroxide. Hydroxide can also be present as a counter ion of the structure directing agent R, as a counter ion of the PDDA cationic polymer, or by the use of aluminum hydroxide as a source of Al. Alternatively, the synthesis mixture may be free from a hydroxide source. Optionally the synthesis mixture comprises a source of hydroxide ions in a $OH^-/Si$ molar ratio of from 0.05 to 1.0, optionally 0.08 to 0.5, for example 0.1 to 0.3, or 0.1 to 0.25, or more than 0.1 to less than 0.18. Preferably the hydroxide ion source is KOH and/or NaOH.

Optionally, the synthesis mixture comprises seed crystals in an amount of from 0.05 to 2, such as 0.1 to 1.5, for example 0.15 to 1 $g_{seed}$/g(silicon source+source of trivalent element X). The optional seed crystals can be of framework type MWW or of any other framework type wherein the synthesis mixture is capable of forming a molecular sieve of MWW framework type. Optionally the seed crystals comprise a molecular sieve of framework type MWW, for example wherein the seed crystals comprise, preferably consist of, MCM-49 and/or MCM-56 zeolite. Optionally, the seed crystals are included in the synthesis mixture in the form of a colloidal suspension in a liquid medium, such as water. As used herein, the expression "colloidal suspension" refers to a suspension containing discrete finely divided particles dispersed in a continuous liquid phase; preferably, it refers to a suspension that is stable, in the sense that no visible separation occurs or sediment forms, in a period sufficient for the use intended, advantageously for at least 10 hours, more advantageously at least 20 hours, preferably at least 100 hours, and more preferably at least 500 hours at ambient temperature (23° C.). The maximum size of the particles for the suspension to remain stable (peptized) will depend to some extent on their shape, and on the nature and pH of the continuous medium, as well as on the period during which the suspension must remain usable. The particles may be spherical, or of other shapes. Where particles are other than spherical, the dimension referred to is their smallest dimension. The colloidal seeds generally have an average diameter (or smallest dimension, corresponding to the number-average primary particle size as determined by SEM for 100 or more particles) of 300 nm or less, in particular of 200 nm or less, more particularly of 100 nm or less, provided that said colloidal seeds form a stable suspension, in the sense that no visible separation occurs or sediment forms, in a period sufficient for the use intended. The production of colloidal seed suspensions and their use in the synthesis of molecular sieves are disclosed in, for example, International Patent Application Publication Nos. WO 00/06493 and WO 00/06494.

The synthesis mixture comprises $H_2O$ and $SiO_2$ in a $H_2O:SiO_2$ molar ratio of from 5 to less than 50, in particular from 5 to 40, more particularly from 10 to 30, such as from 15 to 25.

In a preferred embodiment, the synthesis mixture comprises the structure directing agent R and the alkali or alkaline earth metal cation M source in a R:M molar ratio of less than 2.5, preferably less than 2.0.

Crystallization and Recovery

The crystallization conditions in step (b) of the method include a temperature of from 80° C. to 225° C., preferably from 100° C. to 200° C., more preferably from 140° C. to 180° C., for instance from 150° C. to 170° C., such as from 155° C. to 165° C.

The time required for the crystallization to be carried under will vary. For example, at higher temperatures, the crystallization time may be reduced. Optionally, the crystallization conditions in step (b) of the method include heating for a period of from 1 to about 800 hours, such as from about 10 to less than 600 hours, in particular from about 24 to 140 hours, for example from about 40 to about 90 hours. The crystallization time can be established by methods known in the art such as by sampling the synthesis mixture at various times and determining the yield and x-ray crystallinity of precipitated solid.

Crystallization can be carried out in any suitable reactor vessel, such as, for example, a polypropylene jar or a Teflon® bottle, an acid digestion vessel, a Teflon® lined or stainless steel autoclave, a plough shear mixer, or a reaction kettle, preferably a polypropylene jar, a Teflon® bottle, or a Teflon® lined or stainless steel autoclave.

Optionally, the synthesis mixture is subjected to agitation during step (b), for example the conditions in step (b) include stirring. Optionally, the synthesis mixture is stirred for at least a portion of step (b), such as throughout step (b). Alternatively, the synthesis mixture is not stirred during step (b), i.e. crystallization is carried out under static conditions. Optionally during step (b), the synthesis mixture is heated with agitation provided by a mixing device which moves the mixture in a turbulent fashion such as occurs with a pitch blade turbine mixer. Other means of introducing agitation known to one skilled in the art can be employed, such as pumping the synthesis mixture around the vessel holding the mixture. The purpose of the agitation is to assist mass and heat transfer through the synthesis mixture in a uniform manner. The degree of agitation should be low enough to minimize shear-induced seed formation in the synthesis mixture. Optionally, agitation is stopped once the synthesis mixture reaches a pre-determined set temperature. Optionally, heating of the synthesis mixture continues after the stop of agitation. Alternatively, temperature can be maintained at the temperature reached when agitation was stopped. It will be appreciated that the synthesis mixture may optionally be agitated (e.g. stirred) after step (b). Optionally, the synthesis mixture is subjected to discontinuous stirring while heating, according to which the synthesis mixture may be subjected to a plurality of static crystallization steps separated by agitated crystallization steps. For example, step (b) of the method may be repeated following a step of heating the synthesis mixture under stirred crystallization conditions, said crystallization conditions including a temperature of from 80° C. to 225° C.

Optionally, the crystallization conditions of step (b) include a temperature equal to or greater than the effective nucleation temperature of the synthesis mixture. The effective nucleation temperature can be understood to be the temperature at which continued stirring of the heated zeolite synthesis mixture would result in significant decrease of the mass mean crystal diameter of the product zeolite crystals, e.g., a reduction of the mass mean crystal diameter of the product crystals of 15 percent or greater. Preferably, the temperature of step (b) of the method is a temperature at which, if the synthesis mixture is stirred, stirring will result in a reduction of the mass mean crystal diameter of the product zeolite crystals of less than 10 percent, more preferably less than 5 percent, as compared to the product zeolite crystals obtained from a corresponding unstirred synthesis mixture. It will be appreciated that the effective nucleation temperature of the synthesis mixture will depend on the composition of the synthesis mixture which in turn will be governed by the zeolite being prepared. The effective nucleation temperature can be confirmed by procedures known in the art such as by x-ray detection of crystal presence greater than any seed level. Changes in synthesis mixture viscosity during the first period can also be used to determine the onset of crystallization. The effective nucleation temperature will be a function of the type of zeolite being prepared and may often be expressed as a temperature range rather than a single sharply defined temperature.

Typically, the molecular sieve product is formed in solution and can be recovered by standard means, such as by centrifugation or filtration. The separated product can also be washed, recovered by centrifugation or filtration and dried.

Processing the Molecular Sieve

As a result of the crystallization process, the recovered molecular sieve product contains within its pores at least a portion of the structure directing agent used in the synthesis. Preferably, the method additionally comprises activating the molecular sieve to remove the structure directing agent from the molecular sieve, leaving active sites within the microporous channels of the molecular sieve open for contact with a feedstock. The activation process is typically accomplished by calcining, or essentially heating the molecular sieve comprising the template in the presence of an oxygen-containing gas. In some cases, it may be desirable to heat the molecular sieve in an environment having a low or zero oxygen concentration. This type of process can be used for partial or complete removal of the structure directing agent from the intracrystalline pore system. In other cases, particularly with smaller structure directing agents, complete or partial removal from the sieve can be accomplished by conventional desorption processes. Typically, the recovered molecular sieve is subjected to a calcining step involving heating the material at a temperature of at least about 200° C., preferably at least about 300° C., more preferably at least about 370° C. for at least 1 minute and generally not longer than 20 hours. While subatmospheric pressure can be employed for the thermal treatment, atmospheric pressure is usually desired for reasons of convenience. The thermal treatment can be performed at a temperature up to about 925° C. For instance, the thermal treatment can be conducted at a temperature of from 300 to 600° C., for instance from 400 to 550° C., such as from 500 to 550° C., in the presence of an oxygen-containing gas, for example, in air and/or ozone.

The molecular sieve may also be subjected to an ion-exchange treatment, for example, with aqueous ammonium salts, such as ammonium nitrates, ammonium chlorides, and ammonium acetates, in order to remove remaining alkali metal cations and/or alkaline earth metal cations and to replace them with protons thereby producing the acid form of the molecular sieve. To the extent desired, the original cations of the as-synthesized material, such as alkali metal cations, can be replaced by ion exchange with other cations. Preferred replacing cations can include hydrogen ions, hydrogen precursor, e.g. ammonium ions and mixtures thereof. The ion exchange step may take place after the as-made molecular sieve is dried. The ion-exchange step may take place either before or after a calcination step.

The molecular sieve may also be subjected to other treatments such as steaming and/or washing with solvent. Such treatments are well-known to the skilled person and are carried out in order to modify the properties of the molecular sieve as desired.

Once the molecular sieve has been synthesized, it can be formulated into a product composition by combination with other materials, such as binders and/or matrix materials that provide additional hardness to the finished product. These other materials can be inert or catalytically active materials.

In particular, it may be desirable to incorporate the molecular sieve of the present invention or manufactured by the process of the present invention with another material that is resistant to the temperatures and other conditions employed during use. Such materials include synthetic or naturally occurring zeolites as well as inorganic materials such as clays, silica and/or metal oxides such as alumina, yttria, zirconia, gallium oxide, zinc oxide and mixtures thereof. The metal oxides may be either naturally occurring or in the form of gelatinous precipitates or gels including mixtures of silica and metal oxides. Naturally occurring clays which may be used include the montmorillonite and kaolin family, which families include the subbentonites, and the kaolins commonly known as Dixie, McNamee, Georgia and Florida clays or others in which the main mineral constituent is halloysite, kaolinite, dickite, nacrite, or anauxite. Such clays can be used in the raw state as originally mined or after being subjected to calcination, acid treatment or chemical modification. These binder materials are resistant to the temperatures and other conditions, e.g., mechanical attrition, which occur in various hydrocarbon separation processes. Thus the molecular sieve of the present invention or manufactured by the process of the present invention may be used in the form of an extrudate with a binder. They are typically bound by forming a pill, sphere, or extrudate. The extrudate is usually formed by extruding the molecular sieve, optionally in the presence of a binder, and drying and calcining the resulting extrudate. Further treatments such as steaming, and/or ion exchange may be carried out as required. The molecular sieve may optionally be bound with a binder having a surface area of at least 100 m$^2$/g, for instance at least 200 m$^2$/g, optionally at least 300 m$^2$/g.

These materials may be incorporated into naturally occurring clays, e.g., bentonite and kaolin, to improve the crush strength of the product under commercial operating conditions.

In addition to the foregoing materials, the molecular sieve of the present invention can be composited with a porous matrix material such as silica-alumina, silica-magnesia, silica-zirconia, silica-thoria, silica-beryllia, silica-titania as well as ternary compositions such as silica-alumina-thoria, silica-alumina-zirconia, silica-alumina-magnesia and silica-magnesia-zirconia.

The relative proportions of molecular sieve and inorganic oxide matrix may vary widely, with the molecular sieve content ranging from about 1 to about 100 percent by weight and more usually, particularly when the composite is prepared in the form of extrudates, in the range of about 2 to about 95, optionally from about 20 to about 90 weight percent of the composite.

The Molecular Sieve

The present invention also provides a molecular sieve of MWW framework type obtainable by or made according to the method of the invention.

In a further embodiment, the present invention also provides a molecular sieve of MWW framework type having, in its calcined and anhydrous form, a composition comprising the molar relationship:

$$(n)SiO_2{:}X_2O_3$$

wherein X is a trivalent element selected from aluminum, boron, and/or gallium, preferably wherein X comprises at least aluminum, more preferably wherein X is aluminum, and n is the number of moles of $SiO_2$ per mole of $X_2O_3$ and varies from 8 to less than 30, in particular at least 10, such as at least 12 or at least 14, up to less than 30, such as at most 26 or at most 24. It will be understood that the $Si{:}X_2$ molar ratio is the molar ratio in the molecular sieve framework. Any suitable method can be used to verify the composition of a molecular sieve material, such as inductively coupled plasma optical emission spectrometry (ICP-OES) analysis. Preferably, when X is Al, $^{27}Al$ NMR spectroscopy can be used to determine whether Al detected in a molecular sieve sample is Al incorporated into the molecular sieve framework, or Al deposited on the material as an impurity. It will be appreciated that extra-framework aluminum can be expected to be visible by $^{27}Al$ NMR spectroscopy as a signal having a chemical shift ($\delta$) of around 0 ppm. Framework Al is visible by $^{27}Al$ NMR spectroscopy as a signal having a shift ($\delta$) close to 50 ppm.

The molecular sieve of MWW framework type of the present invention is characterized by a high external surface area together with a high micropore volume.

Advantageously, the molecular sieve of MWW framework type of the present invention has, in its calcined and ion-exchanged form, a micropore volume ($V_{micro}$) of more than 0.13 $cm^3/g$, preferably at least 0.14 $cm^3/g$, more preferably at least 0.15 $cm^3/g$. The micropore volume ($V_{micro}$) of the molecular sieve of MWW framework type is typically at most 0.2 $cm^3/g$, more particularly at most 0.19 $cm^3/g$, such as at most 0.18 $cm^3/g$.

Advantageously, the molecular sieve of MWW framework type of the present invention has, in its calcined and ion-exchanged form, a nitrogen external surface area ($S_{ext}$) (also commonly referred to as mesopore surface area) of at least 125 $m^2/g$, preferably at least 130 $m^2/g$, more preferably at least 135 $m^2/g$, most preferably at least 140 $m^2/g$, such as at least 145 $m^2/g$. The nitrogen external surface area ($S_{ext}$) of the molecular sieve of MWW framework type is typically at most 200 $m^2/g$, more particularly at most 180 $m^2/g$, most particularly at most 165 $m^2/g$, such as at most 160 $m^2/g$.

A suitable method for obtaining $S_{ext}$ and $V_{micro}$ is by application of the t-plot model to the $N_2$ isotherm, as referenced in "Analytical Methods in Fine Particle Technology, P. A. Webb and C. Orr, Micromeritics Instrument Corporation, ISBN 0-9656783-0-X", the contents of which are hereby incorporated by reference.

Optionally, the molecular sieve of MWW framework type of the present invention has, in its calcined and ion-exchanged form, a nitrogen Brunauer-Emmett-Teller (BET) total surface area ($S_{tot}$) of from 250 to 600, such as 300 to 550, for example 400 to 550 $m^2/g$.

Optionally, the molecular sieve of MWW framework type of the present invention has, in its calcined and ion-exchanged form, an $S_{ext}/S_{tot}$ ratio of more than 20%, preferably from 22 to 50%, more preferably from 25 to 35%.

The molecular sieve of MWW framework type of the present invention is characterized by having an XRD pattern including d-spacing maxima at 12.4±0.25, 3.57±0.07 and 3.42±0.07 Angstroms (either calcined or as-synthesized). The MWW family molecular sieve materials may also be characterized by having an XRD pattern including d-spacing maxima at 12.4±0.25, 6.9±0.15, 3.57±0.07 and 3.42±0.07 Angstroms (either calcined or as-synthesized).

Optionally, the molecular sieve of MWW framework type of the present invention has, in its as-synthesized form, an X-ray diffraction pattern characteristic of MCM-49, as shown in Table 1 below:

TABLE 1

| Interplanar d-Spacing (Angstroms) | Relative Intensity $I/I_0 \times 100$ |
|---|---|
| 13.15 ± 0.26 | w-s* |
| 12.49 ± 0.24 | vs |
| 11.19 ± 0.22 | m-s |
| 6.43 ± 0.12 | w |
| 4.98 ± 0.10 | w |
| 4.69 ± 0.09 | w |
| 3.44 ± 0.07 | vs |
| 3.24 ± 0.06 | w |

*shoulder

Optionally, the molecular sieve of MWW framework type of the present invention has, in its calcined form, an X-ray diffraction pattern characteristic of MCM-49, as shown in Table 2 below:

TABLE 2

| Interplanar d-Spacing (Angstroms) | Relative Intensity $I/I_0 \times 100$ |
|---|---|
| 12.41 ± 0.24 | vs |
| 11.10 ± 0.22 | s |
| 8.89 ± 0.17 | m-s |
| 6.89 ± 0.13 | w |
| 6.19 ± 0.12 | m |
| 6.01 ± 0.12 | w |
| 5.56 ± 0.11 | w |
| 4.96 ± 0.10 | w |
| 4.67 ± 0.09 | w |
| 4.59 ± 0.09 | w |
| 4.39 ± 0.09 | w |
| 4.12 ± 0.08 | w |
| 4.07 ± 0.08 | w-m |
| 3.92 ± 0.08 | w-m |
| 3.75 ± 0.07 | w-m |
| 3.57 ± 0.07 | w |
| 3.43 ± 0.07 | s-vs |
| 3.31 ± 0.06 | w |
| 3.21 ± 0.06 | w |
| 3.12 ± 0.06 | w |
| 3.07 ± 0.06 | w |
| 2.83 ± 0.05 | w |
| 2.78 ± 0.05 | w |
| 2.69 ± 0.05 | w |
| 2.47 ± 0.05 | w |
| 2.42 ± 0.05 | w |
| 2.38 ± 0.05 | w |

The Relative Intensities are given in terms of the symbols vs=very strong (60-100), s=strong (40-60), m=medium (20-40) and w=weak (0-20).

It will be understood by a person skilled in the art that the molecular sieve of MWW framework type of the present invention may contain impurities, such as amorphous materials; unit cells having non-MWW framework topologies (e.g., MFI, MTW, MOR, FER, quartz, tridymite or other dense phases that may or may not impact the performance of the resulting catalyst); and/or other impurities (e.g., heavy metals and/or organic hydrocarbons). Typical examples of the non-MWW framework type molecular sieve co-existing with the MWW framework type molecular sieve of the present invention are Kenyaite, EU-1, ZSM-50, ZSM-12, ZSM-48, ZSM-5, Ferrierite, Mordenite, Sodalite, and/or Analcine. Other examples are molecular sieves having framework type of EUO, MTW, FER, MOR, SOD, ANA, and/or MFI. The MWW framework type molecular sieve of the present invention are preferably substantially free of impurities. The term "substantially free of impurities" used herein means the MWW framework type molecular sieve of the present invention preferably contains a minor proportion (less than 50 wt %), preferably less than 20 wt %, more preferably less than 10 wt %, even more preferably less than 5 wt % and most preferably less than 1 wt %, of such impurities (or "non-MWW framework type molecular sieve"), which weight percent (wt %) values are based on the combined weight of impurities and pure phase MWW framework type molecular sieve. The amount of impurities can be appropriately determined by powder XRD, rotating electron diffraction, and/or SEM/TEM (e.g. different crystal morphologies).

Use of the Molecular Sieve

The molecular sieve of MWW framework type of this invention may be used as an adsorbent, such as for separating at least one component from a mixture of components in the vapor or liquid phase having differential sorption characteristics with respect to the molecular sieve. Therefore, at least one component can be partially or substantially totally separated from a mixture of components having differential sorption characteristics with respect to the molecular sieve by contacting the mixture with the molecular sieve to selectively sorb the one component.

The molecular sieve of this invention can be used to catalyze a wide variety of chemical conversion processes including many of present commercial/industrial importance. Examples of chemical conversion processes which are effectively catalyzed by the molecular sieve, by itself or in combination with one or more other catalytically active substances including other crystalline catalysts, include those requiring a catalyst with acid activity. Specific examples include:

(1) alkylation of aromatic hydrocarbons, e.g., benzene, with long chain olefins, e.g., C14 olefin, with reaction conditions including a temperature of from about 340° C. to about 500° C., a pressure of from about atmospheric to about 200 atmospheres, a weight hourly space velocity of from about 2 $hr^{-1}$ to about 2000 $hr^{-1}$ and an aromatic hydrocarbon/olefin mole ratio of from about 1/1 to about 20/1, to provide long chain alkyl aromatics which can be subsequently sulfonated to provide synthetic detergents;

(2) alkylation of aromatic hydrocarbons with gaseous olefins to provide short chain alkyl aromatic compounds, e.g., the alkylation of benzene with ethylene to provide ethylbenzene, with reaction conditions including a temperature of from about 170° C. to about 260° C., a pressure of from about 20 to about 55 atmospheres, and an ethylene alkylating agent weight hourly space velocity (WHSV) of from 0.1 $hr^{-1}$ to about 20 $hr^{-1}$, or the alkylation of benzene with propylene to provide cumene (isopropylbenzene), with reaction conditions including a temperature of from about 10° C. to about 125° C., a pressure of from about 1 to about 30 atmospheres, and an aromatic hydrocarbon weight hourly space velocity (WHSV) of from 5 $hr^{-1}$ to about 50 $hr^{-1}$;

(3) alkylation of reformate containing substantial quantities of benzene and toluene with fuel gas containing C5 olefins to provide, inter alia, mono- and dialkylates with reaction conditions including a temperature of from about 315° C. to about 455° C., a pressure of from about 2860 to about 3550 kPa (about 400 to about 800 psig), a WHSV-olefin of from about 0.4 $hr^{-1}$ to about 0.8 $hr^{-1}$, a WHSV-reformate of from about 1 $hr^{-1}$ to about 2 $hr^{-1}$ and a gas recycle of from about 1.5 to 2.5 vol/vol fuel gas feed;

(4) alkylation of aromatic hydrocarbons, e.g., benzene, toluene, xylene and naphthalene, with long chain olefins, e.g., C14 olefin, to provide alkylated aromatic lube base stocks with reaction conditions including a temperature of from about 160° C. to about 260° C. and a pressure of from about 2515 to 3205 kPa (350 to 450 psig);

(5) alkylation of phenols with olefins or equivalent alcohols to provide long chain alkyl phenols with reaction conditions including a temperature of from about 200° C. to about 250° C., a pressure of from about 1480 to 2170 kPa (200 to 300 psig) and a total WHSV of from about 2 $hr^{-1}$ to about 10 $hr^{-1}$; and (6) alkylation of isoalkanes, e.g., isobutane, with olefins, e.g., 2-butene, with reaction conditions including a temperature of from about −25° C. to about 400° C., e.g., from 75° C. to 200° C., a pressure of from below atmospheric to about 35000 kPa (5000 psig), e.g., from 100 to 7000 kPa (1 to 1000 psig), a weight hourly space velocity based on olefin of from about 0.01 $hr^{-1}$ to about 100 $hr^{-1}$, e.g., from 0.1 $hr^{-1}$ to 20 $hr^{-1}$, and a mole ratio of total isoalkane to total olefin of from about 1:2 to about 100:1, e.g., from 3:1 to 30:1.

EXAMPLES

The present invention is further illustrated below without limiting the scope thereto.

In these examples, the x-ray diffraction (XRD) patterns of the as-synthesized materials were recorded on an X-Ray Powder Diffractometer (Bruker, D8 Discover or STOE, Stadi P Combi) using copper K-α radiation in the 2θ range of 2 to 40 degrees.

The scanning electron microscopy (SEM) images of the as-synthesized materials were obtained on a FEI Company, Helios Nanolab G3 UC Scanning Electron Microscope.

Zeolite framework types of the as-synthesized materials were identified by comparison of their XRD patterns to those of known zeolite materials. SEM images were used to aid assessment of product purity—the presence of obviously different crystal morphologies in a SEM image can be an indication of impurities in the form of other crystalline materials. Such an approximate analysis can be especially useful in identifying the presence of formation of relatively minor amounts of crystalline impurities which may not be identifiable on product XRD patterns.

The solid state $^{27}Al$ MAS NMR spectra (1 pulse) were recorded on a Bruker Avance III-HD 500 spectrometer (11.7 T) operating at 130.3 MHz. The measurements were done using zirconia rotors of 4 mm outer diameter spun at 14 kHz. MAS NMR spectra were obtained with a π/12 pulse and a recycle delay of Is. Chemical shifts were referenced to 1 M Al $(NO_3)_3$ solution. The samples were hydrated over night before the analysis.

The density of the powder materials, in as-synthesized and dried form, was measured using a pycnometer. Pycnometer was weighed empty then was filled with water to determine the exact volume. An exact know amount of the material was added in the pycnometer which was then filled with water. Air trapped in between the powder materials was removed by placing the pycnometer in a sonic bath. The material was allowed to settle until the top liquor was clear. The pycnometer was then filled with water and weighed. The volume of the powder was determined based on the weight difference and density was calculated based on the weight and the volume.

The following measurements were conducted on samples that were ion-exchanged and calcined. For each sample subjected to ion-exchange and calcination, the procedure used was as follows: the as-prepared sample was washed two times with a 1M ammonium nitrate solution and then calcined at 537° C. for 10 hours.

The $SiO_2$:$Al_2O_3$ molar ratios of the materials were determined by inductively coupled plasma (ICP) method.

The overall BET surface area ($S_{tot}$) of the materials was determined by the BET method as described by S. Brunauer, P. H. Emmett and E. Teller, *J. Am. Chem. Soc.,* 1938, 60, 309, incorporated herein by reference, using nitrogen adsorption-desorption at liquid nitrogen temperature.

The micropore volume ($V_{micro}$) of the materials was determined by application of the t-plot model to the $N_2$ isotherm, as referenced in "Analytical Methods in Fine Particle Technology, P. A. Webb and C. Orr, Micrometrics Instrument Corporation, ISBN 0-9656783-0-X", the contents of which are hereby incorporated by reference.

Physisorption isotherms were collected according to the method disclosed in "Analytical Methods in Fine Particle Technology", P. A. Webb and C. Orr, Micrometrics Instrument Corporation ISBN 0-9656783-0-X, the contents of which are incorporated herein by reference.

Comparative Examples 1 and 2 illustrate the preparation of MCM-49 and MCM-56 zeolites respectively. Examples 3 to 5 illustrate the preparation of a molecular sieve of MWW framework type according to the process of the present invention, using various amounts of PDDA. Comparative Examples 6 and 7 were prepared according to the synthesis method of Example 3 but in the presence of a higher amount of PDDA.

Comparative Example 1—MCM-49 Zeolite

A sodium aluminate solution was prepared by dissolving sodium aluminate powder in water (23.5 wt % alumina, 19.4 wt % sodium oxide). 18891.0 mg water, 1192.4 mg of the sodium aluminate solution, 89.6 mg of a sodium hydroxide solution (40.0 wt %), 3779.3 mg precipitated silica (Ultrasil® VN3), and 1047.7 mg of a hexamethyleneimine solution (99.0 wt %) were added to a Teflon® liner. The mixture was stirred for 5 min after each addition and for 10 min after the last addition. The mixture was then treated under hydrothermal conditions at 160° C. for 60 h while stirring with a U-shaped impeller. The solid material was recovered afterwards, washed several times with water, and dried at 120° C.

The synthesis mixture was as follows (synthesis mixture/ molar ratios):

$Si/Al_2$:20.84,M/Si:0.15,R/Si:0.18,$H_2O$/Si:19.02.

XRD was used to identify the recovered material as MCM-49.

Comparative Example 2—MCM-56 Zeolite

A sodium aluminate solution was prepared by dissolving sodium aluminate powder in water (23.5 wt % alumina, 19.4 wt % sodium oxide). 18986.0 mg water, 1332.1 mg of the sodium aluminate solution, 183.8 mg MCM-56 seeds (20.0 wt %), 3846.5 mg precipitated silica (Ultrasil® VN3), and 651.6 mg of a hexamethyleneimine solution (99.0 wt %)

were added to a Teflon® liner. The mixture was stirred for 5 min after each addition and for 10 min after the last addition. The mixture was then treated under hydrothermal conditions at 160° C. for 60 h while stirring with a U-shaped impeller. The solid material was recovered afterwards, washed several times with water, and dried at 120° C.

The synthesis mixture was as follows (synthesis mixture/ molar ratios, excluding seed crystals):

$Si/Al_2$:19.01,M/Si:0.14,R/Si:0.11,$H_2O$/Si:18.94.

The amount of seed crystals used was 0.95 wt % [$g_{seed}$ ($g_{SiO2}$+$g_{Al2O3}$)$^{-1}$].

XRD was used to identify the recovered material as MCM-56.

Example 3—MWW-Type Zeolite (0.10 wt % PDDA Chloride)

A sodium aluminate solution was prepared by dissolving sodium aluminate powder in water (10.1 wt % alumina, 7.3 wt % sodium oxide). 17097.3 mg water, 2784.5 mg of the sodium aluminate solution, 172.5 mg of a sodium hydroxide solution (40.0 wt %), 125.0 mg PDDA chloride (average Mw 200,000-350,000, 20 wt %), 3774.4 mg precipitated silica (Ultrasil® VN3), and 1046.3 mg of a hexamethyleneimine solution (99.0 wt %) were added to a Teflon® liner. The mixture was stirred for 5 min after each addition, except after PDDA addition that was for 15 min, and for 10 min after the last addition. The mixture was then treated under hydrothermal conditions at 160° C. for 60 h while stirring with a U-shaped impeller. The solid material was recovered afterwards, washed several times with water, and dried at 120° C.

The synthesis mixture was as follows (synthesis mixture/ molar ratios):

$Si/Al_2$:20.84,M/Si:0.15,R/Si:0.18,$H_2O$/Si:19.02.

The amount of PDDA chloride used was 0.10 wt %, based on the weight of the synthesis mixture.

XRD was used to identify the recovered material as an MWW-type zeolite.

Example 4—MWW-Type Zeolite (0.30 wt % PDDA Chloride)

A sodium aluminate solution was prepared by dissolving sodium aluminate powder in water (10.0 wt % alumina, 7.3 wt % sodium oxide). 16468.8 mg water, 2797.8 mg of the sodium aluminate solution, 172.1 mg of a sodium hydroxide solution (40.0 wt %), 750.3 mg PDDA chloride (average Mw 200,000-350,000 g/mol, 10 wt %), 3766.8 mg precipitated silica (Ultrasil® VN3), and 1044.2 mg of a hexamethyleneimine solution (99.0 wt %) were added to a Teflon® liner. The mixture was stirred for 5 min after each addition, except after PDDA addition that was for 15 min, and for 10 min after the last addition. The mixture was then treated under hydrothermal conditions at 160° C. for 60 h while stirring with a U-shaped impeller. The solid material was recovered afterwards, washed several times with water, and dried at 120° C.

The synthesis mixture was as follows (synthesis mixture/ molar ratios):

$Si/Al_2$:20.84,M/Si:0.15,R/Si:0.18,$H_2O$/Si:19.02.

The amount of PDDA chloride used was 0.30 wt %, based on the weight of the synthesis mixture.

XRD was used to identify the recovered material as an MWW-type zeolite.

Example 5—MWW-Type Zeolite (0.70 wt % PDDA Chloride)

A sodium aluminate solution was prepared by dissolving sodium aluminate powder in water (10.1 wt % alumina, 7.3 wt % sodium oxide). 16394.0 mg water, 2767.8 mg of the sodium aluminate solution, 171.4 mg of a sodium hydroxide solution (40.0 wt %), 875.0 mg PDDA chloride (average Mw 200,000-350,000, 20 wt %), 3751.7 mg precipitated silica (Ultrasil® VN3), and 1040.0 mg of a hexamethylene-imine solution (99.0 wt %) were added to a Teflon® liner. The mixture was stirred for 5 min after each addition, except after PDDA addition that was for 15 min, and for 10 min after the last addition. The mixture was then treated under hydrothermal conditions at 160° C. for 60 h while stirring with a U-shaped impeller. The solid material was recovered afterwards, washed several times with water, and dried at 120° C.

The synthesis mixture was as follows (synthesis mixture/molar ratios):

$$Si/Al_2:20.84,M/Si:0.15,R/Si:0.18,H_2O/Si:19.02.$$

The amount of PDDA chloride used was 0.70 wt %, based on the weight of the synthesis mixture.

XRD was used to identify the recovered material as an MWW-type zeolite.

Comparative Example 6 (1.00 wt % PDDA Chloride)

A sodium aluminate solution was prepared by dissolving sodium aluminate powder in water (10.1 wt % alumina, 7.3 wt % sodium oxide). 16042.3 mg water, 2759.4 mg of the sodium aluminate solution, 170.9 mg of a sodium hydroxide solution (40.0 wt %), 1250.0 mg PDDA chloride (average Mw 200,000-350,000, 20 wt %), 3740.4 mg precipitated silica (Ultrasil® VN3), and 1036.9 mg of a hexamethylene-imine solution (99.0 wt %) were added to a Teflon® liner. The mixture was stirred for 5 min after each addition, except after PDDA addition that was for 15 min, and for 10 min after the last addition. The mixture was then treated under hydrothermal conditions at 160° C. for 60 h while stirring with a U-shaped impeller. The solid material was recovered afterwards, washed several times with water, and dried at 120° C.

The synthesis mixture was as follows (synthesis mixture/molar ratios):

$$Si/Al_2:20.84,M/Si:0.15,R/Si:0.18,H_2O/Si:19.02.$$

The amount of PDDA chloride used was 1.00 wt %, based on the weight of the synthesis mixture.

MWW phase did not crystallize at a PDDA chloride concentration of 1.00 wt %.

Comparative Example 7 (2.00 wt % PDDA Chloride)

A sodium aluminate solution was prepared by dissolving sodium aluminate powder in water (10.1 wt % alumina, 7.3 wt % sodium oxide). 14870.2 mg water, 2731.6 mg of the sodium aluminate solution, 169.2 mg of a sodium hydroxide solution (40.0 wt %), 2500.0 mg PDDA chloride (average Mw 200,000-350,000, 20 wt %), 3702.6 mg precipitated silica (Ultrasil® VN3), and 1026.4 mg of a hexamethyleneimine solution (99.0 wt %) were added to a Teflon® liner. The mixture was stirred for 5 min after each addition, except after PDDA addition that was for 15 min, and for 10 min after the last addition. The mixture was then treated under hydrothermal conditions at 160° C. for 60 h while stirring with a U-shaped impeller. The solid material was recovered afterwards, washed several times with water, and dried at 120° C.

The synthesis mixture was as follows (synthesis mixture/molar ratios):

$$Si/Al_2:20.84,M/Si:0.15,R/Si:0.18,H_2O/Si:19.02.$$

The amount of PDDA chloride used was 2.00 wt %, based on the weight of the synthesis mixture.

MWW phase did not crystallize at a PDDA chloride concentration of 2.00 wt %.

Analysis of Crystalline Material Products

FIG. 1 shows XRD spectra of Comparative Examples 1-2 and Examples 3-5, in their as-synthesized form. The XRD pattern of Comparative Example 1 shows peaks typical of MCM-49; the XRD pattern of Comparative Example 2 shows peaks typical of MCM-56; and the XRD patterns of Examples 3-5 show peaks typical of molecular sieves of MWW framework type. As compared to the XRD pattern of Comparative Example 1 (MCM-49), the XRD pattern of Comparative Example 2 (MCM-56) shows broader, often merged, peaks. Without wishing to be bound by theory, it is believed that these differences are indicative of the predominance of disordered lamellae in MCM-56, as compared to the more regularly stacked layers present in MCM-49. Most notably, the XRD pattern of MCM-49 material shows two separate peaks clearly identifiable at around 8 and 10 (2θ), while that of MCM-56 shows a broad merged peak in the same region (as is shown by comparison of the XRD spectra for Comparative Examples 1 and 2). For a more detailed discussion of characteristic XRD patterns of MCM-56 as compared to, e.g., MCM-49, see U.S. Pat. Nos. 5,362,697, 5,827,491, and 5,453,554, the contents of which are incorporated herein by reference. The XRD patterns of Examples 3 and 4 are similar to that of MCM-49 (Comparative Example 1). The XRD pattern of Example 5 shows broader peaks as compared to Examples 3-4. The XRD patterns of Comparative Examples 1-2 and Examples 3-5 also show that impurity phases are not detected.

FIGS. 2a-2e show Scanning Electron Microscopy (SEM) images of each of Comparative Examples 1-2 and Examples 3-5. The SEM images show that morphology of Examples 3 and 4 is similar to that of MCM-49 (Comparative Example 1). For Example 5, SEM images show some minor amorphous phase so, without being bound by theory, it is believed that higher PDDA concentration may inhibit or slow down the crystallization so that at higher PDDA concentration, crystallization time should be extended. Variations in morphology, for example resulting from the presence of impurities and/or an amorphous phase, are not visible in the SEM images of any examples. Thus, for all examples, SEM analysis suggests the formation of a single zeolite structure.

Figure 3:
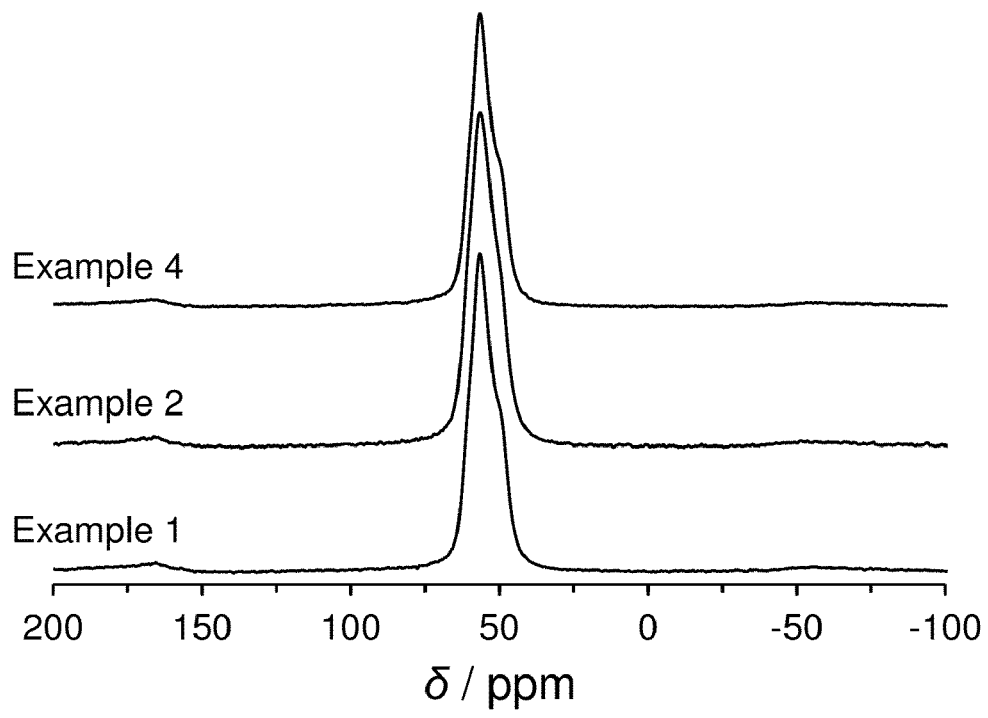
FIG. 3 shows $^{27}Al$ NMR spectra of Comparative Examples 1-2 and Example 4.

FIG. 3 shows $^{27}$Al NMR spectra of Comparative Examples 1-2 and Example 4. In all spectra, a substantial peak is observed at around 50 ppm. A chemical shift (δ) close to 50 ppm is characteristic of Al incorporated into a zeolite framework. None of the spectra show a peak in the region of about 0 ppm, which would be indicative of extra-framework Al. Thus, $^{27}$Al NMR spectroscopy analysis suggests that the Al detected by ICP-OES analysis is framework Al, indicating that the inventive method has successfully incorporated Al into the zeolite framework.

Figure 4:
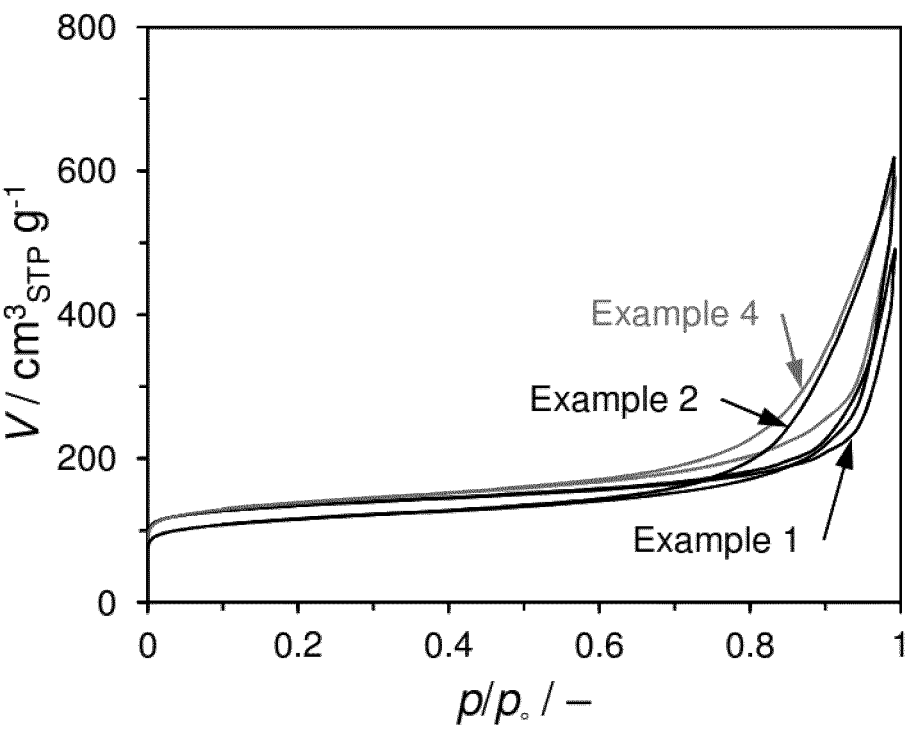
FIG. 4 shows $N_2$ physisorption isotherms of Comparative Examples 1-2 and Example 4.

FIG. 4 shows the $N_2$ physisorption isotherms of Comparative Examples 1-2 and Example 4, after ion-exchange and calcination. The physisorption isotherm of Comparative Example 1 (MCM-49) differs from that of Comparative Example 2 (MCM-56) in that the isotherm for MCM-56 shows a strong hysteresis loop, which re-joins the initial curve at about 4.8 p/p$^0$. It is believed that the large, pronounced hysteresis loop of MCM-56, which is indicative of significantly delayed desorption of $N_2$ from the zeolite as p/p$^0$ is reduced back from 1 to 0, is evidence for MCM-56 having a different mesopore shape to that of MCM-49. As can be seen from FIG. 4, $N_2$ physisorption isotherm of Example 4 is more similar to that of MCM-56 (Comparative Example 2). Consequently, it is believed that the mesopore shape of the MWW molecular sieve of Example 4 is more similar to that of MCM-56.

FIG. 5 shows the thermogravimetric analysis of as-prepared Comparative Example 1 and Example 4. It can be seen from FIG. 5 that Example 4 has about 2 wt % higher weight loss as compared with Comparative Example 1, which can be attributed to the decomposition of PDDA at 400-600° C.

Table 3 shows the Si:Al$_2$ molar ratio, after ion-exchange and calcination, and the textural and chemical properties, after ion-exchange and calcination (total surface area, mesopore surface area, ratio of mesopore surface area to total surface area, and micropore volume), of Comparative Examples 1-2 and Examples 3-5.

TABLE 3

| Sample | Si:Al$_2$ molar ratio | $S_{tot}$ (m$^2$/g) | $S_{ext}$ (m$^2$/g) | $S_{ext}/S_{tot}$ (%) | $V_{micro}$ (cm$^3$/g) |
|---|---|---|---|---|---|
| Comparative Example 1 (MCM-49) | 18 | 508 | 102 | 20 | 0.17 |
| Comparative Example 2 (MCM-56) | 17 | 384 | 123 | 32 | 0.13 |
| Example 3 | — | 516 | 146 | 28 | 0.15 |
| Example 4 | 20 | 515 | 152 | 29 | 0.15 |
| Example 5 | — | 370 | 164 | 44 | 0.09 |

As indicated by the results in Table 3, Examples 3-4 are characterized by a high external surface area (or mesopore surface area) in combination with a high micropore volume. More particularly, the total surface area ($S_{tot}$) and external surface area ($S_{ext}$) of Examples 3-4 is significantly higher than the total surface area and external surface area of MCM-49 and MCM-56 (Comparative Examples 1-2), while the $S_{ext}/S_{tot}$ ratio of Examples 3-4 is close to the $S_{ext}/S_{tot}$ ratio of MCM-56 (Comparative Example 2) and, at the same time, the micropore volume of Examples 3-4 is preserved and closer to the micropore volume of MCM-49 (Comparative Example 1). The lower $V_{micro}$ value obtained for Example 5 may be due to some minor amorphous phase present in the product. As already mentioned, without being bound by theory, it is believed that higher PDDA concentration may inhibit or slow down the crystallization so that at higher PDDA concentration, crystallization time should be extended.

In summary, the presence of PDDA in the synthesis mixture is accompanied by changes in total surface area, external surface area (or mesopore surface area) and microporosity, providing a molecular sieve of MWW framework type with a layered structure showing an increased total surface area and an increased external surface area (or mesopore surface area), while preserving or increasing microporosity. This is especially advantageous as accessibility to surface pockets of MWW-type molecular sieves is of significant importance for their catalytic performance, for instance in applications such as aromatic alkylation while preserving or increasing microporosity is fundamental to shape selective catalysis with molecular sieves.

Comparative Example 8 and Example 9—Formulated Extrudates Comprising Molecular Sieves Prepared According to Comparative Example 1 and Example 4

Portions of Comparative Example 1 and of Example 4 were formed into $\frac{1}{20}^{th}$ inch quadrulobe extrudates according to the following method, corresponding to Comparative Example 8 and Example 9. Eighty (80) parts by weight of zeolite (respectively of Comparative Example 1 Example 4) were combined with 20 parts Versal-300 alumina, on a dry weight basis, to form a dry powder. The dry powder was placed in a miller or a mixer and mixed for about 5 to 15 minutes. Sufficient water was added to the powder during the mixing process to produce an extrudable paste. The extrudable paste was formed into a $\frac{1}{20}^{th}$ inch quadrulobe extrudate using a ram extruder. After extrusion, the $\frac{1}{20}^{th}$ inch quadrulobe extrudate was dried at a temperature of about 120° C. The dried extrudate was then calcined in nitrogen to a temperature between 454° C. and 593° C. and cooled under nitrogen flow. The extrudates were then charged to an exchange column, humidified, and exchanged with ammonium nitrate. After washing the extrudates with water, they were calcined under a flow of air between 454° C. and 593° C.

The dried extrudates were tested for collidine uptake according to the following method. The collidine uptake of the extrudate zeolite compositions was determined as the micromoles of collidine (a type of catalyst poison) absorbed per gram of composition sample that is dried under nitrogen flow at 200° C. for 60 minutes on a Thermogravametric Analyzer. After drying the catalyst sample, the collidine was sparged over the catalyst sample for 60 minutes at a collidine partial pressure of 3 torr. The sample was then flushed with nitrogen for 60 minutes. The collidine uptake was calculated from the following formula: (sample weight after sparging with collidine−dried catalyst sample weight)÷(molecular weight of collidine×dried catalyst sample weight). When the sample weight and the dried sample weight is measured in grams, the molecular weight of collidine is $121.2 \times 10^{-4}$ grams per micromole.

Table 4 shows measured collidine uptake of the extrudates of Comparative Example 8 and Example 9. Collidine (2,4,6-trimethylpyridine) is a relatively large molecule having an aromatic ring core, and so uptake of collidine can provide an indication of the proportion of acid sites located in mesopores accessible to larger molecules. It is believed that catalysts that exhibit high collidine uptake are likely to be effective in alkylation of larger molecules, especially single-ring aromatic molecules. Having a larger number of surface acid sites accessible to larger molecules may allow the catalyst to continue to provide an acceptable level of activity for a longer period of time.

TABLE 4

| Sample | $N_{collidine}$ ($\mu$mol/g) |
|---|---|
| Comparative Example 8 (based on MCM-49 of Example 1) | 108.5 |
| Example 9 (based on MWW-type of Example 4) | 130.8 |

As shown by the results in Table 4, collidine uptake is significantly higher in Example 9 vs. Comparative Example 8. This can be correlated to a greater mesoporosity for the molecular sieve of MWW framework type of the present invention (as illustrated by Example 4) compared to MCM-49 materials (as illustrated by Comparative Example 1). This is also representative of an increased proportion of acid sites located in mesopores accessible to larger molecules and an improved alkylation activity of larger molecules, especially single-ring aromatic molecules.

The dried extrudates were also tested for benzene alkylation activity and selectivity according to the following method. 0.5 g of catalyst extrudates were charged to an isothermal well-mixed Parr autoclave reactor along with a mixture comprising of 156 g benzene and 28 g propylene under nitrogen atmosphere. The reaction was carried out at 130° C. and 2170 kPa (300 psig) for four hours under nitrogen atmosphere. Small samples of product were withdrawn at regular intervals and analysed by gas chromatography. The catalyst performance was assessed by a kinetic activity rate constant based on propylene conversion and isopropyl benzene (cumene) selectivity at 100% propylene conversion.

Table 5 shows the catalytic properties of the extrudates of Comparative Example 8 and Example 9, in particular the pseudo $2^{nd}$ order rate constant (k), the di-isopropylbenzene to isopropylbenzene (cumene) selectivity ($S_{DIPB/IPB}$) and the tri-isopropylbenzene to isopropylbenzene (cumene) selectivity ($S_{TIPB/IPB}$).

TABLE 5

| Sample | k (cm$^3$ mol$^{-1}$ h$^{-1}$ g$^{-1}$) | $S_{DIPB/IPB}$ | $S_{TIPB/IPB}$ |
|---|---|---|---|
| Comparative Example 8 (based on MCM-49 of Example 1) | 510 | 21.6 | 3.17 |
| Example 9 (based on MWW-type of Example 4) | 462 | 15.7 | 1.49 |

As can be seen from Table 5, the inventive extrudates of Example 9 show significantly lower selectivities to undesired di- and tri-isopropylbenzene by-products compared to the extrudates of Comparative Example 8 based on MCM-49, while the $2^{nd}$ order rate constant (k) remains similar.

While the present invention has been described and illustrated with reference to particular embodiments, it will be appreciated by those of ordinary skill in the art that the invention lends itself to many different variations not specifically illustrated herein.

Where in the foregoing description, integers or elements are mentioned which have known, obvious or foreseeable equivalents, then such equivalents are herein incorporated as if individually set forth. Reference should be made to the claims for determining the true scope of the present invention, which should be construed so as to encompass any such equivalents. It will also be appreciated by the reader that integers or features of the invention that are described as preferable, advantageous, convenient or the like are optional and do not limit the scope of the independent claims. Moreover, it is to be understood that such optional integers or features, whilst of possible benefit in some embodiments of the invention, may not be desirable, and may therefore be absent, in other embodiments. All numerical values within the detailed description herein are modified by "about" the indicated value, and take into account experimental error and variations that would be expected by a person having ordinary skill in the art.

Additionally or alternately, the invention relates to:

Embodiment 1: A method of synthesizing a molecular sieve of MWW framework type, the method comprising the steps of:

a) preparing a synthesis mixture capable of forming a molecular sieve of MWW framework type, said synthesis mixture comprising water, a silicon source, a source of a trivalent element X, a structure directing agent R, a source of alkali or alkaline earth metal cation M, a source of poly(diallyldimethyl ammonium) cation (PDDA), optionally a source of a pentavalent element Z, optionally a source of hydroxide ions, and optionally seed crystals, the synthesis mixture having the following molar ratio composition:

Si:X$_2$=8 to less than 30,

H$_2$O:Si=5 to less than 50,

M:Si=0.05 to 1.0,

R:Si=0.05 to 1.0, wherein the source of PDDA is added in an amount of from 0.01 to less than 1.0 wt % based on the weight of synthesis mixture;

b) heating said synthesis mixture under crystallization conditions for a time sufficient to form crystals of said molecular sieve of MWW framework type, said crystallization conditions including a temperature of from 80° C. to 225° C.; and c) recovering said crystals of the molecular sieve of MWW framework type from the synthesis mixture.

Embodiment 2: The method of embodiment 1, wherein the source of PDDA is selected from at least one of PDDA chloride and PDDA hydroxide, in particular PDDA chloride.

Embodiment 3: The method of embodiment 1 or 2, wherein the synthesis mixture contains the PDDA source in an amount of 0.05 to 0.7 wt %, preferably 0.05 to less than 0.7%, based on the weight of synthesis mixture.

Embodiment 4: The method of any preceding embodiments, wherein the structure directing agent R is selected from the group consisting of cyclopentylamine, cyclohexylamine, cycloheptylamine, hexamethyleneimine (HMI), heptamethyleneimine, homopiperazine, pentamethonium bromide or hydroxide, hexamethonium bromide or hydroxide, heptamethonium bromide or hydroxide, and combinations thereof, preferably wherein the structure directing agent R is hexamethyleneimine (HMI).

Embodiment 5: The method of any preceding embodiments, wherein X is selected from the group consisting of aluminum, boron, gallium, and mixtures thereof, preferably wherein X comprises at least aluminum, more preferably wherein X is aluminum.

Embodiment 6: The method of any preceding embodiments, wherein the source of trivalent element X comprises Al$_2$O$_3$, preferably wherein the source of a trivalent element X is Al$_2$O$_3$.

Embodiment 7: The method of any preceding embodiments, wherein the silicon source comprises SiO$_2$, preferably wherein the silicon source is SiO$_2$.

Embodiment 8: The method of any preceding embodiments, wherein Z, if present, is phosphorus.

Embodiment 9: The method of any one of embodiments 1 to 7, wherein the synthesis mixture does not contain any pentavalent element Z.

Embodiment 10: The method of any preceding embodiments, wherein M is selected from the group consisting of sodium, potassium, lithium, rubidium, calcium, magnesium and mixtures thereof, preferably sodium and/or potassium, more preferably sodium.

Embodiment 11: The method of any preceding embodiments, wherein the synthesis mixture comprises the alkali metal or alkaline earth metal cation M source in a M:Si molar ratio of from 0.08 to 0.5, more particularly from 0.1 to 0.3, such as from more than 0.1 to less than 0.18.

Embodiment 12: The method of any preceding embodiments, wherein the OH⁻ source, if present, comprises an alkali metal hydroxide, an alkaline earth metal hydroxide, ammonium hydroxide, aluminum hydroxide, a hydroxide form of the structure directing agent R, a hydroxide form of PDDA, or a combination thereof.

Embodiment 13: The method of any preceding embodiments, wherein the synthesis mixture comprises a source of hydroxide ions in a OH⁻:Si molar ratio of from 0.05 to 1.0, preferably from 0.08 to 0.5, more preferably from 0.1 to 0.3, such as from 0.1 to 0.25.

Embodiment 14: The method of any preceding embodiments, wherein the synthesis mixture comprises R and M in a R:M molar ratio of less than 2.5, preferably less than 2.0.

Embodiment 15: The method of any preceding embodiments, wherein the synthesis mixture comprises molecular sieve seed crystals in an amount of from 0.05 to 2 $g_{seed}$/g (silicon source+source of trivalent element X).

Embodiment 16: The method of embodiment 15, wherein the seed crystals comprise a molecular sieve of MWW framework type, preferably MCM-49 and/or MCM-56.

Embodiment 17: The method of any preceding embodiments, wherein the crystallization conditions in step (b) include a temperature of from 100° C. to 200° C., preferably from 140° C. to 180° C.

Embodiment 18: The method of any preceding embodiments, wherein the crystallization conditions in step (b) include heating for a period of from 1 to 800 hours, especially from 10 to less than 600 hours, in particular from 24 to 140 hours, for example from 60 to 90 hours.

Embodiment 19: A molecular sieve of MWW framework type, obtainable by the method of any one of embodiments 1 to 18.

Embodiment 20: A molecular sieve of MWW framework type, having, in its calcined and anhydrous form:

a composition comprising the molar relationship:

$$(n)SiO_2:X_2O_3$$

wherein X is a trivalent element selected from the group consisting of aluminum, boron, gallium, and mixtures thereof, preferably wherein X comprises at least aluminum, more preferably wherein X is aluminum, and n is the number of moles of $SiO_2$ per mole of $X_2O_3$ and varies from 8 to less than 30;

an external surface area ($S_{ext}$) of at least 125 m²/g; and a micropore volume ($V_{micro}$) of at more than 0.13 cm³/g.

Embodiment 21: The molecular sieve of embodiment 19 or 20, having a ratio of external surface area to BET total surface area ($S_{ext}/S_{tot}$) of more than 20%, preferably from 22 to 50%, more preferably from 25 to 35%.

Embodiment 22: Use of the molecular sieve of any one of embodiments 19 to 21 in a hydrocarbon chemical conversion process, in particular wherein the hydrocarbon chemical conversion process is alkylation reaction, more particularly aromatic alkylation.

The invention claimed is:

1. A method of synthesizing a molecular sieve of MWW framework type, the method comprising the steps of:

a) preparing a synthesis mixture capable of forming a molecular sieve of MWW framework type, said synthesis mixture comprising water, a silicon source, a source of a trivalent element X, a structure directing agent R, a source of alkali or alkaline earth metal cation M, a source of poly(diallyldimethyl ammonium) cation (PDDA), optionally a source of a pentavalent element Z, optionally a source of hydroxide ions, and optionally seed crystals, the synthesis mixture having the following molar ratio composition:

Si:$X_2$=8 to less than 30, $H_2O$:Si=5 to less than 50,

M:Si=0.05 to 1.0,

R:Si=0.05 to 1.0, wherein the source of PDDA is added in an amount of from 0.01 to less than 1.0 wt % based on the weight of synthesis mixture;

b) heating said synthesis mixture under crystallization conditions for a time sufficient to form crystals of said molecular sieve of MWW framework type, said crystallization conditions including a temperature of from 80° C. to 225° C.; and c) recovering said crystals of the molecular sieve of MWW framework type from the synthesis mixture.

2. The method according to claim 1, wherein the PDDA source is selected from at least one of PDDA chloride and PDDA hydroxide, and wherein the PDDA source is added to the synthesis mixture in an amount of 0.05 to 0.7 wt %, based on the weight of synthesis mixture.

3. The method according to claim 1, wherein the structure directing agent R is selected from the group consisting of cyclopentylamine, cyclohexylamine, cycloheptylamine, hexamethyleneimine (HMI), heptamethyleneimine, homopiperazine, pentamethonium bromide or hydroxide, hexamethonium bromide or hydroxide, heptamethonium bromide or hydroxide, and combinations thereof.

4. The method according to claim 3, wherein the structure directing agent R is hexamethyleneimine (HMI).

5. The method according to claim 1, wherein X is selected from the group consisting of aluminum, boron, gallium, and mixtures thereof.

6. The method according to claim 5, wherein the source of trivalent element X comprises $Al_2O_3$.

7. The method according to claim 1, wherein the silicon source comprises $SiO_2$.

8. The method according to claim 1, wherein Z is present and is phosphorus.

9. The method according to claim 1, wherein the synthesis mixture does not contain any pentavalent element Z.

10. The method according to claim 1, wherein M is selected from the group consisting of sodium, potassium, lithium, rubidium, calcium, magnesium and mixtures thereof.

11. The method according to claim 1, wherein the synthesis mixture comprises the alkali metal or alkaline earth metal cation M source in a M:Si molar ratio of from 0.08 to 0.5.

12. The method according to claim 1, wherein the OH⁻ source is present and comprises an alkali metal hydroxide, an alkaline earth metal hydroxide, ammonium hydroxide, aluminum hydroxide, a hydroxide form of the structure directing agent R, a hydroxide form of PDDA, or a combination thereof.

13. The method according to claim 1, wherein the synthesis mixture comprises a source of hydroxide ions in a OH⁻:Si molar ratio of from 0.05 to 1.0.

14. The method according to claim 1, wherein the synthesis mixture comprises R and M in a R:M molar ratio of less than 2.5.

15. The method according to claim 1, wherein the synthesis mixture comprises molecular sieve seed crystals in an amount of from 0.05 to 2 gseed/g (silicon source+source of trivalent element X).

16. The method according to claim 1, wherein the crystallization conditions in step (b) include a temperature of from 100° C. to 200° C., and wherein the crystallization conditions in step (b) include heating for a period of from 1 to 800 hours.

17. A molecular sieve of MWW framework type, obtainable by the method of claim 1.

\* \* \* \* \*